United States Patent
Vitek et al.

(10) Patent No.: US 6,593,512 B1
(45) Date of Patent: Jul. 15, 2003

(54) TRANSGENIC MOUSE EXPRESSING HUMAN TAU GENE

(75) Inventors: Michael P. Vitek, Apex, NC (US); Hana N. Dawson, Morrisville, NC (US); Jeanne F. Loring, Foster City, CA (US)

(73) Assignee: Cognosci, Inc., Research Triangle Park, NC (US)

( * ) Notice: Subject to any disclaimer, the term of this patent is extended or adjusted under 35 U.S.C. 154(b) by 0 days.

(21) Appl. No.: 09/517,431

(22) Filed: Mar. 2, 2000

Related U.S. Application Data

(60) Provisional application No. 60/122,691, filed on Mar. 3, 1999.

(51) Int. Cl.$^7$ .................. G01N 33/00; A01K 67/00; C12N 15/00; C12N 15/74; C12N 5/00
(52) U.S. Cl. .................. 800/18; 800/3; 800/9; 800/12; 800/21; 800/22; 435/455; 435/463; 435/320.1; 435/325
(58) Field of Search .............................. 800/3, 8, 9, 11, 800/13, 18, 12, 21, 22; 424/93.21; 435/325, 4, 455, 463, 320.1

(56) References Cited

U.S. PATENT DOCUMENTS

| | | | |
|---|---|---|---|
| 5,569,824 A | 10/1996 | Donehower et al. | 800/10 |
| 5,569,827 A | 10/1996 | Kessous-Elbaz et al. | 800/11 |
| 5,703,209 A | 12/1997 | Vitek et al. | 530/350 |
| 5,767,337 A | 6/1998 | Roses et al. | 800/3 |
| 6,374,130 B1 | 4/2002 | Reiman | 600/407 |
| 2002/0010947 A1 | 1/2002 | Gurney et al. | 800/12 |
| 2002/0018995 A1 | 2/2002 | Ghetti et al. | 435/6 |
| 2002/0026651 A1 | 2/2002 | Hutton et al. | 800/18 |

FOREIGN PATENT DOCUMENTS

| | | |
|---|---|---|
| WO | WO 01/53340 A2 | 7/2001 |

OTHER PUBLICATIONS

Wall; Transgenic Livestock: Progress and Prospects for the Future, 1996, Theriogenology 45: 57–68.*

Brion et. al.; Transgenic Expression of the Shortest Human Tau Affects Its Compartmentalization and Its Phosphorylation as in the Pretangle Stage of Alzheimer's Disease, 1999, American Journal of Pathology vol. 154, No. 1: 255–270.*

Gotz et. al.; Somatodendritic Localization and hyperphosphorylation of tau protein in transgenic mice expressing the longest human brain tau isoform, 1995, The EMBO Journal vol. 14, No. 7: 1304–1313.*

"Tau Mutations Directory", Jennifer Kwon, MD, Washington University, St. Louis, www.alzforum.com, Feb. 9, 2000.

Dawson et al, "Inhibition of neuronal maturation in primary hippocampal neurons from tau deficient mice", *Journal of Cell Science*, 114(6) 1179–1187, 2001.

Clark et al., Pathogenic implications of mutations in the tau gene in pallido–ponto–nigral degeneration and related neuro–degenerative disorders linked to chromosome 17, *Proc. Nat'l. Acad. Sci.*, vol. 95, pp. 13103–13107, Oct., 1998.

Yamaoka et al., "Linkage of frontotemporal dementia to chromosome 17: clinical and neuropathological characterization in phenotype," Amer. J. of Human Genetics, 1996 Dec., 59 (6), 1306–12.

Spillantini et al., "Mutation in the tau gene in familial multiple system tauopathy with presenile dementia," *Proc. Nat'l Acad. Sci USA*, 1998, 95: 7737–7741.

Poorkaj et al., "Tau is a candidate gene for chromosome 17 frontotemporal dementia," *Ann. Neurol.*, 1998, 43:815–825.

Hutton et al., Association of missense and 5'–splice–site mutations in tau with the inherited dementia FTDP–17, *Nature*, 1998, 393: 702–705.

* cited by examiner

*Primary Examiner*—Deborah Crouch
*Assistant Examiner*—Thai-An N. Ton
(74) *Attorney, Agent, or Firm*—Morgan, Lewis & Bockius LLP

(57) ABSTRACT

A bigenic mouse is provided whose germ cells and somatic cells contain (i) inactive mouse TAU genes, and/or (ii) a transgene encoding the human TAU gene, with the transgene including all regulatory elements of the human TAU gene necessary for neuronal expression of the transgene in the bigenic mouse, and/or for human patterns of expression of the transgene in the bigenic mouse. The mice of the invention may contain one or two alleles for the human TAU gene (i.e., one or two TAU alleles). Mice of the invention are useful as a source of human Tau protein, and are useful as a model of Alzheimer's, Frontal Temporal Dementia and Parkinson's-like diseases.

19 Claims, 3 Drawing Sheets

SEQUENCE LISTING

<160> NUMBER OF SEQ ID NOS: 22

<210> SEQ ID NO 1
<211> LENGTH: 739
<212> TYPE: DNA
<213> ORGANISM: Homo sapiens

<400> SEQUENCE: 1
ctcgagggcc ggccacgtgg aaggccgctc aggacttctg taggagagga caccgcccca      60

-continued

```
ggctgactga aagtaaaggg cagcggacca gcggcggagc cactggcctt gccgcatggc    120
ccgaaggagg acacccaccc ccgcaacgac acaaagactc caactacagg aggtggagaa    180
agcgcgtgcg ccacggaagc gcgtgcgcgc gcggtcagcg ccgcggcctg aggcgtagcg    240 ggaggggggac cgcgaaaggg cagcgccgag aggaacgagc cgggagacgc cggacggccg    300
agcggcaggg cgctcgcgcg cccactagtg gccggaggag aaggcccgc ggaggccgcg    360 ctgcccgccc cctcccctgg ggaggctcgc gttcccgctg ctcgcgcctg ccgcccgccg    420
gcctcaggaa cgcgccctct cgccgcgcgc gccctcgcag tcaccgccac ccaccagctc    480
cggcaccaac agcagcgccg ctgccaccgc ccaccttctg ccgccgccac cacagccacc    540
ttctcctcct ccgctgtcct ctcccgtcct cgcctctgtc gagtatcagg tgaactttga    600
accaggatgg ctgagccccg ccaggagttc gaagtgatgg aagatcacgc tgggacgtac    660
gggttggggg acaggaaaga tcaggggggc tacaccatgc accaagacca agagggtgac    720
acggacgctg gcctgaaag                                                 739
```

<210> SEQ ID NO 2
<211> LENGTH: 21
<212> TYPE: DNA
<213> ORGANISM: Homo sapiens

<400> SEQUENCE: 2

```
ccgcaacgac acaaagactc c                                              21
```

<210> SEQ ID NO 3
<211> LENGTH: 21
<212> TYPE: DNA
<213> ORGANISM: Homo sapiens

<400> SEQUENCE: 3

```
gaggagaagg tggctgtggt g                                              21
```

<210> SEQ ID NO 4
<211> LENGTH: 22
<212> TYPE: DNA
<213> ORGANISM: Homo sapiens

<400> SEQUENCE: 4

```
ttggcacttc gatgatgacc tc                                             22
```

<210> SEQ ID NO 5
<211> LENGTH: 22
<212> TYPE: DNA
<213> ORGANISM: Homo sapiens

<400> SEQUENCE: 5

```
cattgtgacg tgtgatgagg gg                                             22
```

<210> SEQ ID NO 6
<211> LENGTH: 36
<212> TYPE: DNA
<213> ORGANISM: Homo sapiens

<400> SEQUENCE: 6

```
acgtacgggt tgggggacag gaaagatcag ggggc                               36
```

<210> SEQ ID NO 7
<211> LENGTH: 2796
<212> TYPE: DNA

<213> ORGANISM: Homo sapiens

<400> SEQUENCE: 7

| | | | | | |
|---|---|---|---|---|---|
| cctcccctgg | ggaggctcgc | gttcccgctg | ctcgcgcctg | ccgcccgccg | gcctcaggaa | 60 |
| cgcgccctct | cgccgcgcgc | gccctcgcag | tcaccgccac | ccaccagctc | cggcaccaac | 120 |
| agcagcgccg | ctgccaccgc | ccaccttctg | ccgccgccac | cacagccacc | ttctcctcct | 180 |
| ccgctgtcct | ctcccgtcct | cgcctctgtc | gactatcagg | tgaactttga | accaggatgg | 240 |
| ctgagccccg | ccaggagttc | gaagtgatgg | aagatcacgc | tgggacgtac | gggttggggg | 300 |
| acaggaaaga | tcagggggc | tacaccatgc | accaagacca | agagggtgac | acggacgctg | 360 |
| gcctgaaaga | atctcccctg | cagacccccca | ctgaggacgg | atctgaggaa | ccgggctctg | 420 |
| aaacctctga | tgctaagagc | actccaacag | cggaagatgt | gacagcaccc | ttagtggatg | 480 |
| agggagctcc | cggcaagcag | gctgccgcgc | agccccacac | ggagatccca | gaaggaacca | 540 |
| cagctgaaga | agcaggcatt | ggagacaccc | ccagcctgga | gacgaagct | gctggtcacg | 600 |
| tgacccaagc | tcgcatggtc | agtaaaagca | agacgggac | tggaagcgat | gacaaaaaag | 660 |
| ccaagggggc | tgatggtaaa | acgaagatcg | ccacaccgcg | gggagcagcc | cctccaggcc | 720 |
| agaagggcca | ggccaacgcc | accaggattc | cagcaaaaac | cccgcccgct | ccaaagacac | 780 |
| cacccagctc | tggtgaacct | ccaaaatcag | gggatcgcag | cggctacagc | agccccggct | 840 |
| ccccaggcac | tccggcagc | cgctcccgca | ccccgtccct | tccaaccccca | cccaccggg | 900 |
| agcccaagaa | ggtggcagtg | gtccgtactc | cacccaagtc | gccgtcttcc | gccaagagcc | 960 |
| gcctgcagac | agcccccgtg | cccatgccag | acctgaagaa | tgtcaagtcc | aagatcggct | 1020 |
| ccactgagaa | cctgaagcac | cagccgggag | gcgggaaggt | gcagataatt | aataagaagc | 1080 |
| tggatcttag | caacgtccag | tccaagtgtg | gctcaaagga | taatatcaaa | cacgtcccgg | 1140 |
| gaggcggcag | tgtgcaaata | gtctacaaac | cagttgacct | gagcaaggtg | acctccaagt | 1200 |
| gtggctcatt | aggcaacatc | catcataaac | aggaggtgg | ccaggtggaa | gtaaaatctg | 1260 |
| agaagcttga | cttcaaggac | agagtccagt | cgaagattgg | gtccctggac | aatatcaccc | 1320 |
| acgtccctgg | cggaggaaat | aaaaagattg | aaacccacaa | gctgaccttc | cgcgagaacg | 1380 |
| ccaaagccaa | gacagaccac | ggggcggaga | tcgtgtacaa | gtcgccagtg | gtgtctgggg | 1440 |
| acacgtctcc | acggcatctc | agcaatgtct | cctccaccgg | cagcatcgac | atggtagact | 1500 |
| cgccccagct | cgccacgcta | gctgacgagg | tgtctgcctc | cctggccaag | cagggttttgt | 1560 |
| gatcaggccc | ctggggcggt | caataattgt | ggagaggaga | gaatgagaga | gtgtggaaaa | 1620 |
| aaaaagaata | atgacccggc | cccgccctc | tgccccage | tgctcctcgc | agttcggtta | 1680 |
| attggttaat | cacttaacct | gcttttgtca | ctcggctttg | gctcgggact | tcaaaatcag | 1740 |
| tgatgggagt | aagagcaaat | ttcatctttc | caaattgatg | ggtgggctag | taataaaata | 1800 |
| tttaaaaaaa | aacattcaaa | aacatggcca | catccaacat | ttcctcaggc | aattcctttt | 1860 |
| gattcttttt | tcttccccct | ccatgtagaa | gaggagaag | gagaggctct | gaaagctgct | 1920 |
| tctgggggat | ttcaagggac | tgggggtgcc | aaccacctct | ggccctgttg | tgggggttgt | 1980 |
| cacagaggca | gtggcagcaa | caaaggattt | gaaaactttg | gtgtgttcgt | ggagccacag | 2040 |
| gcagacgatg | tcaaccttgt | gtgagtgtga | cgggggttgg | ggtggggcgg | gaggccacgg | 2100 |
| gggaggccga | ggcaggggct | gggcagaggg | gaggaggaag | cacaagaagt | gggagtggga | 2160 |
| gaggaagcca | cgtgctggag | agtagacatc | cccctccttg | ccgctgggag | agccaaggcc | 2220 |
| tatgccacct | gcagcgtctg | agcggccgcc | tgtccttggt | ggccggggt | ggggccctgc | 2280 |

```
tgtgggtcag tgtgccaccc tctgcagggc agcctgtggg agaagggaca gcgggttaaa    2340
aagagaaggc aagcctggca ggagggttgg cacttcgatg atgacctcct tagaaagact    2400
gaccttgatg tcttgagagc gctggcctct tcctccctcc ctgcaggta gggcgcctga     2460 gcctaggcgg ttccctctgc tccacagaaa ccctgtttta ttgagttctg aaggttggaa    2520
ctgctgccat gattttggcc actttgcaga cctgggactt tagggctaac cagttctctt    2580
tgtaaggact tgtgcctctt gggagacgtc cacccgtttc caagcctggg ccactggcat    2640
ctctggagtg tgtgggggtc tgggaggcag gtcccgagcc cctgtccttt cccacggcca    2700
ctgcagtcac cccgtctgcg ccgctgtgct gttgtctgcc gtgagagccc aatcactgcc    2760 tataccccctc atcacacgtc acaatgtccc gaattc                             2796
```

<210> SEQ ID NO 8
<211> LENGTH: 792
<212> TYPE: DNA
<213> ORGANISM: Homo sapiens

<400> SEQUENCE: 8

```
ctcgagggcc ggccacgtgg aaggccgctc aggacttctg taggagagga caccgcccca    60
ggctgactga aagtaaaggg cagcggacca gcggcggagc cactggcctt gccccgaccc    120
cgcatggccc gaaggaggac acccaccccc gcaacgacac aaagactcca actacaggag    180
gtggagaaag cgcgtgcgcc acggaagcgc gtgcgcgcgc ggtcagcgcc gcggcctgag    240
gcgtagcggg aggggaccg cgaaagggca gcgccgagag gaacgagccg ggagacgccg     300
gacggccgag cggcagggcg ctcgcgcgcc cactagtggc cggaggagaa ggccccgcgg    360
aggccgcgct gcccgccccc tccctgggg aggctcgcgt tcccgctgct cgcgcctgcc    420
gcccgccggc tcaggaacg cgccctctcg ccgcgcgcgc cctcgcagtc accgccaccc    480
accagctccg gcaccaacag cagcgccgct gccaccgccc accttctgcc gccgccacca    540
cagccacctt ctcctcctcc gctgtcctct cccgtcctcg cctctgtcga ctatcaggta    600
agcgccgcgg ctccgaaatc tgcctcgccg tccgcctctg tgcacccctg cgccgccgcc    660
cctcgccctc cctctccgca gactgggct tcgtgcgccg ggcatcggtc ggggccaccg     720
cagggcccct ccctgcctcc cctgctcggg ggctggggcc agggcggcct ggaaagggca    780
cctgagcaag gg                                                        792
```

<210> SEQ ID NO 9
<211> LENGTH: 259
<212> TYPE: DNA
<213> ORGANISM: Homo sapiens

<400> SEQUENCE: 9

```
ctctctctct cttcacccca ctctgccccc caacactcct cagaacttat cctctcctct    60
tctttcccca ggtgaacttt gaaccaggat ggctgagccc cgccaggagt tcgaagtgat    120
ggaagatcac gctgggacgt acgggttggg ggacaggaaa gatcaggggg gctacaccat    180
gcaccaagac caagagggtg acacggacgc tggcctgaaa ggttagtgga cagccatgca    240
cagcaggccc agatcactg                                                 259
```

<210> SEQ ID NO 10
<211> LENGTH: 593
<212> TYPE: DNA
<213> ORGANISM: Homo sapiens

```
<400> SEQUENCE: 10
ttggtccctt tgtgggtttg ttgcagggcg tgttccagct gttttccacag ggagcgattt      60 tcagctccac aggacactgc tccccagttc ctcctgagaa caaaagggg gcgctgggga       120 gaggccaccg ttctgagggc tcactgtatg tgttccagaa tctcccctgc agaccccac      180 tgaggacgga tctgaggaac cgggctctga acctctgat gctaagagca ctccaacagc      240
ggaaggtggg ccccccttca gacgcccct ccatgcctcc agcctgtgct tagccgtgct      300
ttgagcctcc ctcctggctg catctgctgc tcccctggc tgagagatgt gctcactcct      360
tcggtgcttt gcaggacagc gtggtgggag ctgagccttg cgtcgatgcc ttgcttgctg      420
gtgctgagtg tgggcacctt catcccgtgt gtgctctgga ggcagccacc cttggacagt      480
ccggcgcaca gctccacaaa gccccggtcc atacgattgt cctcccacac cccttcaaa      540 agccccctcc ctcctctctt tcttcagggg ccagtaggtc agagcagcca ttt             593

<210> SEQ ID NO 11
<211> LENGTH: 706
<212> TYPE: DNA
<213> ORGANISM: Homo sapiens

<400> SEQUENCE: 11
gggagaagtc ttggaagtca cctagagatg acactgccat tttgcagatg aggaaaccgt      60
ccaatcaaaa tggaccaagg acttgcccaa agcctcacag caaaaccata ggccccgca     120 ctaaccccag agtccctgtg ctgtcttaag aatcaaatag ttgtaagcaa tcatctggtt      180
ttcagtattt cttcttttaa aatgcctggg gccatgcagc agtctgtttc actgcagcgt      240
ttacacaggg ctgccgggct ttcctggtgg atgagctggg cgttcatgag ccagaaccac      300
tcagcagcat gtcagtgtgc ttcctgggga gactggtagc aggggctccg ggcctacttc      360
agggctgctt tctggcatat ggctgatccc ctcctcactc ctcctccctg cattgctcct      420
gcgcaagaag caaaggtgag gggctgggta tggctcgtcc tggcccctct aaggtggatc      480
tcggtggttt ctagatgtga cagcacccct agtggatgag ggagctcccg gcaagcaggc      540
tgccgcgcag ccccacacgg agatcccaga aggaaccaca ggtgagggta agccccagag      600 accccaggc agtcaaggcc ctgctgggtg cccagctga cctgtgacag aagtgaggga      660
gctttgcgtg tttatcctcc tgtggggcag gaacatgggt ggattc                     706

<210> SEQ ID NO 12
<211> LENGTH: 447
<212> TYPE: DNA
<213> ORGANISM: Homo sapiens

<400> SEQUENCE: 12
gaactcctca gcaatgacat ttgcagagaa gccagagctg agggcaacct tggtattctt      60
gggatgtgaa ctttcctgaa tgtttaaggg aaaatgcccg aaggtacaga gagcttggtt     120
tctagtaaat aataactgtc ttgcttttac ccccccttcat ttgctgacac atacaccagc     180
tgaagaagca ggcattggag acacccccag cctggaagac gaagctgctg gtcacgtgac     240
ccaaggtcag tgaactggaa ttgcctgcca tgacttgggg gttgggggga gggacatggg     300
gtgggctctg cctgaaaaga tcatttggac ctgagctcta attcacaagt ccaggagatt     360
ttagggagtt ggttcttatc aaaggttggc tactcagata tagaaagccc tagtggtttt     420
tttctaatac catttctggg tatcatg                                          447
```

<210> SEQ ID NO 13
<211> LENGTH: 954
<212> TYPE: DNA
<213> ORGANISM: Homo sapiens

<400> SEQUENCE: 13

```
gactgggccg agaagggtcc ggcctttccg aagcccgcca ccactgcgta tctccacaca      60
gagcctgaaa gtggtaaggt ggtccaggaa ggcttcctcc gagagccagg ccccccaggt     120
ctgagccacc agctcatgtc cggcatgcct ggggctcccc tcctgcctga gggcccaga     180
gaggccacac gccaaccttc ggggacagga cctgaggaca cagagggcgg ccgccacgcc     240
cctgagctgc tcaagcacca gcttctagga gacctgcacc aggaggggcc gccgctgaag     300
ggggcagggg gcaaagagag gccggggagc aaggaggagg tggatgaaga ccgcgacgtc     360
gatgagtcct ccccccaaga ctcccctccc tccaaggcct ccccagccca agatgggcgg     420
cctccccaga cagccgccag agaagccacc agcatcccag gcttcccagc ggagggtgcc     480
atcccccctcc ctgtggattt cctctccaaa gtttccacag agatcccagc ctcagagccc     540
gacgggccca gtgtagggcg ggccaaaggg caggatgccc ccctggagtt cacgtttcac     600
gtggaaatca cacccaacgt gcagaaggag caggcgcact cggaggagca tttgggaagg     660
gctgcatttc caggggcccc tggagagggg ccagaggccc ggggcccctc tttgggagag     720
gacacaaaag aggctgacct tccagagccc tctgaaaagc agcctgctgc tgctccgcgg     780
gggaagcccg tcagccgggt ccctcaactc aaaggtctgt gtcttgagct tcttcgctcc     840
ttccctgggg acctcccagg cctcccaggc tgcgggcact gccactgagc ttccaggcct     900
cccgactcct gctgcttctg acgttcctag gacgccacta atcgacacc tggg      954
```

<210> SEQ ID NO 14
<211> LENGTH: 180
<212> TYPE: DNA
<213> ORGANISM: Homo sapiens

<400> SEQUENCE: 14

```
tggctttctg tgaacagtga aaatggagtg tgacaagcat tcttatttta tattttatca      60
gctcgcatgg tcagtaaaag caaagacggg actggaagcg atgacaaaaa agccaaggta     120
agctgacgat gccacggagc tctgcagctg gtcaagttta cagagaagct gtgctttatg     180
```

<210> SEQ ID NO 15
<211> LENGTH: 457
<212> TYPE: DNA
<213> ORGANISM: Homo sapiens

<400> SEQUENCE: 15

```
gagcccgtct caaaaagaaa aagcaaaaga aaagaactg tgattgggag gaacggtcaa      60
cttttcctgtt cttactgatc agaagggata ttaagggtac ctgattcaaa cagcctggag     120
tacactgact ttcaaccatt acctgcctta tttatttta gttactgtcc ttttttcagt     180
ttgtttccct cctccatgtg ctgactttta ttttgatttt atttatgttt atgtttaaga     240
catccacacg ttcctctgct aaaaccttga aaataggcc ttgccttagc cccaaactcc     300
ccactcctg tagctcagac cctctgatcc aaccctccag ccctgctgtg tgcccagagc     360
caccttcctc tcctaaacac gtctcttctg tcacttcccg aactggcagt tctggagcaa     420
aggagatgaa actcaaggta aggaaactct ttgaaaa      457
```

<210> SEQ ID NO 16

<211> LENGTH: 271
<212> TYPE: DNA
<213> ORGANISM: Homo sapiens

<400> SEQUENCE: 16

```
tctaggaggc caagggtcac cccagtctta gccacgtttt gagtcaaggt ggcggagtgg      60
ggctggtgtt acgtcttggt ggcagtaact tttcccaatg gtgaaaaacc cctctatcat     120
gtttcattta caggggctg atggtaaaac gaagatcgcc acaccgcggg gagcagcccc      180
tccaggccag aagggccagg ccaacgccac caggattcca gcaaaaaccc cgcccgctcc     240
aaagacacca cccagctctg gtaagaagaa c                                    271
```

<210> SEQ ID NO 17
<211> LENGTH: 150
<212> TYPE: DNA
<213> ORGANISM: Homo sapiens

<400> SEQUENCE: 17

```
gaaggactca ttaaggccct gtttaagcct gatgataata aggctttcgt ggattttttct    60
ctttaagcga ctaagcaagt ccagagaaga ccaccccctg cagggcccag atctgagaga    120
ggtactcggg agcctactcg ctgggagcag                                      150
```

<210> SEQ ID NO 18
<211> LENGTH: 637
<212> TYPE: DNA
<213> ORGANISM: Homo sapiens
<220> FEATURE:
<221> NAME/KEY: misc_feature
<222> LOCATION: (1)..(637)
<223> OTHER INFORMATION: n can be a or c or g or t

<400> SEQUENCE: 18

```
gagctcagag aggggaagtt acttgtctga ggccacacag cttgttggag cccatctctt      60
gacccaaaga ctgtggagcc gagttggcac ctctctggga gcgggtattg gatggtggtt     120
gatggttttc cattgctttc ctgggaaagg ggtgtctctg tccctccgca aaaaggacag     180
ggaggaagag atgcttcccc agggcnnnng tctgctgtac gtgcgcttcc aacctggctt     240
ccacctgcct aacccagtgg tgagcctggg aatggaccca cggacaggn nnccccaggg     300
cctttttctga ccccacccac tcgagtcctg gcttcactcc cttccttcct tcccaggtga   360
acctccaaaa tcaggggatc gcagcggcta cagcagcccc ggctcccag gcactccgg      420
cagccgctcc cgcaccccgt cccttccaac cccacccacc cgggagccca agaaggtggc    480
agtggtccgt actccaccca gtcgccgtc ttccgcaag agccgcctgc agacagcccc     540
cgtgcccatg ccagacctga gaatgtcaa gtccaagatc ggctccactg agaacctgaa    600
gcaccagccg ggaggcggga aggtgagagt ggctggc                              637
```

<210> SEQ ID NO 19
<211> LENGTH: 222
<212> TYPE: DNA
<213> ORGANISM: Homo sapiens

<400> SEQUENCE: 19

```
cgagcaagca gcgggtccag ggtggcgtgt cactcatcct tttttctggc taccaaaggt     60
gcagataatt aataagaagc tgatcttag caacgtccag tccaagtgtg gctcaaagga    120
taatatcaaa cacgtcccgg gaggcggcag tgtgagtacc ttcacacgtc ccatgcgccg   180
tgctgtggct tgaattatta ggaagtggtg tgagtcgtac ac                       222
```

<210> SEQ ID NO 20
<211> LENGTH: 246
<212> TYPE: DNA
<213> ORGANISM: Homo sapiens

<400> SEQUENCE: 20

```
ttgctcattc tctctcctcc tctctcatct ccaggtgcaa atagtctaca aaccagttga      60
cctgagcaag gtgacctcca agtgtggctc attaggcaac atccatcata aaccaggtag     120
ccctgtggaa ggtgagggtt gggacgggag ggtgcagggg gtggaggagt cctggtgagg     180
ctggaactgc tccagacttc agaagaggct ggaaaggata ttttaggtag acctacatca     240
aggaaa                                                                246
```

<210> SEQ ID NO 21
<211> LENGTH: 200
<212> TYPE: DNA
<213> ORGANISM: Homo sapiens

<400> SEQUENCE: 21

```
ccacagaacc acagaagatg atggcaagat gctcttgtgt gtgttgtgtt ctaggaggtg      60
gccaggtgga agtaaaatct gagaagcttg acttcaagga cagagtccag tcgaagattg     120
ggtccctgga caatatcacc cacgtccctg gcggaggaaa taaaaggta aaggggtag      180
ggtgggttgg atgctgcctt                                                 200
```

<210> SEQ ID NO 22
<211> LENGTH: 1498
<212> TYPE: DNA
<213> ORGANISM: Homo sapiens

<400> SEQUENCE: 22

```
ctttctctgg cacttcatct caccctccct cccttcctct tcttgcagat tgaaacccac      60
aagctgacct tccgcgagaa cgccaaagcc aagacagacc acgggcggga gatcgtgtac     120
aagtcgccag tggtgtctgg ggacacgtct ccacggcatc tcagcaatgt ctcctccacc     180
ggcagcatcg acatggtaga ctcgccccag ctcgccacgc tagctgacga ggtgtctgcc     240
tccctggcca agcagggttt tgtgatcagg ccctggggcg gtcaataatt gtggagagga     300
gagaatgaga gagtgtggaa aaaaaagaa taatgacccg gccccgccc tctgccccca      360
gctgctcctc gcagttcggt taattggtta atcacttaac ctgcttttgt cactcggctt     420
tggctcggga cttcaaaatc agtgatggga gtaaagcaa atttcatctt tccaaattga     480
tgggtgggct agtaataaaa tatttaaaaa aaaacattca aaaacatggc cacatccaac     540
atttcctcag gcaattcctt ttgattcttt tttcttcccc ctccatgtag aagagggaga     600
aggagaggct ctgaaagctg cttctggggg atttcaaggg actggggtg ccaaccacct     660
ctggccctgt tgtgggggtt gtcacagagg cagtggcagc aacaaggat ttgaaaactt     720
tggtgtgttc gtggagccac aggcagacga tgtcaacctt gtgtgagtgt gacggggtt     780
ggggtggggc gggaggccac gggggaggcc gaggcagggg ctgggcagag gggaggagga     840
agcacaagaa gtgggagtgg gagaggaagc cacgtgctgg agagtagaca tccccctcct     900
tgccgctggg agagccaagg cctatgccac ctgcagcgtc tgagcggccg cctgtccttg     960
gtggccgggg gtggggggcct gctgtgggtc agtgtgccac cctctgcagg gcagcctgtg    1020
ggagaaggga cagcgggtta aaaagagaag gcaagcctgg caggagggtt ggcacttcga    1080
```

```
tgatgacctc cttagaaaga ctgaccttga tgtcttgaga gcgctggcct cttcctccct   1140
ccctgcaggg tagggcgcct gagcctaggc ggttccctct gctccacaga aaccctgttt   1200
tattgagttc tgaaggttgg aactgctgcc atgattttgg ccactttgca gacctgggac   1260
tttagggcta accagttctc tttgtaagga cttgtgcctc ttgggagacg tccacccgtt   1320
tccaagcctg ggccactggc atctctggag tgtgtggggg tctgggaggc aggtcccgag   1380
ccccctgtcc ttcccacggc cactgcagtc acccgtctg cgccgctgtg ctgttgtctg   1440
ccgtgagagc ccaatcactg cctataccc tcatcacacg tcacaatgtc ccgaattc    1498
```

TRANSGENIC MOUSE EXPRESSING HUMAN TAU GENE

This application claims priority to provisional application Serial No. 60/122,691, filed Mar. 3, 1999, and which is incorporated herein by reference.

This invention was made with Government support under Grant No. AG13839 awarded by the National Institutes of Health. The Government may have rights in this invention.

BACKGROUND OF THE INVENTION

1. Field of the Invention

The present invention concerns transgenic animals that are useful as models of Alzheimer's disease, other neurodegenerative diseases, and methods of use thereof.

2. Description of the Related Art

Currently affecting some 4,000,000 Americans, Alzheimer's Disease (AD) is the leading cause of dementia and the fourth leading cause of death. Over a typical 10 to 20 year course, AD is characterized by progressive memory loss and the eventual death of the patient. These behaviors are associated with the presence of amyloid plaques, cerebrovascular amyloid deposits and neurofibrillary tangle lesions in the patients' brains. Multiple genes have been associated with familial and sporadic forms of Alzheimer's indicating that different genes can initiate changes that culminate in this rather uniform phenotype.

Existing therapies are palliative and provide only temporary symptomatic relief for a small portion of those afflicted with the disease. At present, there are no effective therapies to slow or halt the progression of the disease thus creating a large unmet medical need for afflicted patients, their families and care givers. Further compounding this picture, the prevalence of Alzheimer's increases with age such that about half of all persons age 85 and older have AD. As our health care system continues to improve the health of Americans, the numbers of Alzheimer's patients will continue to rise in accord with their increased lifespan.

As discussed by Jennifer Kwon at the Alzheimer's Research Forum web page, Tau is a microtubule associated protein that is involved in microtubule assembly and stabilization in the human brain. In adult human brain, six tau isoforms are produced from a single gene by alternative mRNA splicing. They differ from each other by the presence or absence of 29- or 58-amino-acid inserts located in the amino-terminal half and 31-amino-acid repeats located in the carboxy-terminal half. Inclusion of the latter, which is encoded by exon 10 of the tau gene, gives rise to the three tau isoforms that each have four repeats. In normal cerebral cortex, there is a slight preponderance of 3-repeat over 4-repeat tau isoforms. These repeats and some adjoining sequences constitute the microtubule-binding domain of tau (Goedert et al., 1998, Nat Med, April 1999, 5(4): 454–7).

One of the characteristics of AD is the presence of neurofibrillary tangles, intraneuronal deposits of paired helical filaments made of hyperphosphorylated Tau. Abnormal deposit of Tau is also seen in other neurodegenerative disorders, including progressive supranuclear palsy (PSP), corticobasal ganglionic degeneration (CBD), and frontotemporal dementias (FTD) (synonomous with Frontal Temporal Dementias). Variability in the tau gene has been shown to be a risk factor for PSP (Conrad et al., Ann Neurol, February 1997, 41(2): 277–81). Recent studies suggest that mutations of the TAU gene (responsible for coding for the Tau protein) may be involved in these Tau protein abnormalities, possibly contributing to the onset of some of these neurodegenerative disorders.

Pathologically, frontotemporal atrophy is a consistent finding, which may be accompanied by basal ganglia atrophy and substantia nigra depigmentation. Many families have tau-positive inclusions either in neurons or in neurons and glia. And where linkage data was available, familial forms of FTD were linked to chromosome 17. A consensus conference decided that the term FTD with parkinsonism linked to chromosome 17 (FTDP-17) was preferred as it stressed the common clinical and pathologic features shared by this autosomal-dominant, neurodegenerative condition (Foster et al., Ann Neurol, June 1997, 41(6): 706–15).

In 1998, a series of papers reported that mutations in tau were associated with FTDP-17 (Hutton et al., Nature, June 1998, 393(6686): 702–5; Poorjak et al., Ann Neurol, June 1998, 43(6): 815–25; and Spillantini et al., Proc Natl Acad Sci U S A, April 1997, 94(8): 4113–8). The mutations causing various forms of FTD are of two major types (Goedert et al., 1998), coding mutations and intronic mutations. Most coding mutations occur in the microtubule-binding repeat region or very close to it. These potentially lead to a partial loss of function of tau with reduced tau binding to microtubules (Hong et al., Science, December 1998, 282(5395): 1914–7; Dayanandan et al., FEBS Lett, March 1999, 446(2–3): 228–32; Hasegawa et al., FEBS Lett, October 1998, 437(3): 207–10; Goedel et al., 1998; and Spillantini and Goedert, Trends Neurosci October 1998; 21(10):428–33). There is also convincing evidence that tau missense mutations directly increase the tendency of tau to aggregate into filaments (Nacharaju et al., FEBS Lett, March 1999, 447(2–3): 195–9; and Goedert et al., FEBS Lett, May 1999, 450(3): 306–11). Some missense mutations (G272V in exon 9, V337M in exon 12 and R406W in exon 13) affect all isoforms produced, while P301L only alters those isoforms with four repeats. The intronic mutations are all near the splice donor site of the intron following exon 10. By presumably destabilizing a predicted RNA stem-loop, there is a change in the ratio of 3-repeat to 4-repeat isoforms (Hutton et al., 1998; Spillantini, Murrell et al., Proc Natl Acad Sci U S A, June 1998, 95(13): 7737–41). There are two coding mutations, N279K and S305N, which appear to enhance splicing of exon 10 rather than to reduce microtubule assembly (D'Souza et al., Proc Natl Acad Sci U S A, May 1999, 96(10): 5598–603; Hasegawa et al., FEBS Lett, January 1999, 443(2): 93–6). Conversely, the delK280 mutation reduces splicing (D'Souza et al. 1999).

Although the various mutations in tau are associated with frontotemporal dementia, distinctive clinical and pathologic features seem to be found with particular mutations. It is clear that the variable tau isoform content in FTDP-17 tangles is largely explained by the nature of the mutations: Mutations in or near exon 10 result in tangles consisting predominantly of 4-repeat tau, while mutations outside exon 10 are associated with tangles with both 4-repeat and 3-repeat tau. These latter tangles seem to result in filament morphology that is very similar to that seen in Alzheimer's disease. The filament morphology of 4-repeat tangles is more variable but generally they have a longer periodicity than the PHFs seen in AD. Mutations in exon 10 generate glial inclusions and those outside exon 10 generally do not (but there is at least one exception, in press).

Improved assays of the functional effects of tau mutations may enable us to link the size of these effects to the severity of the clinical phenotype. It already seems likely that a large effect on microtubule-binding and tau aggregation correlates with a more severe phenotype. In addition, the exon 10 splice site mutations appear to relate to clinical phenotype based on the degree to which they disrupt splicing (the +16 mutation appears to be the mildest with incomplete penetrance, while the +3 and +14 are most severe). It is, therefor, desirable to be able to provide a mammalian model for testing the effect of the human TAU gene and its mutations on neurodegenerative physiology and behavior.

In this regard, U.S. Pat. No. 5, 767,337 to Roses et al. describes the creation of human apolipoprotein-E, isoform-specific transgenic mice in apolipoprotein-E deficient, knockout mice. These mice are useful as an animal model of one type of Alzheimer's disease. Nevertheless, because of the complexity of this disease and/or syndrome, there remains a need for additional animal models of Alzheimer's disease, and other neurodegenerative diseases.

SUMMARY OF THE INVENTION

Accordingly, it is a purpose of the present invention to provide an animal model for analyzing Alzheimer's, Frontal Temporal Dementia, Parkinson-like, and other neurodegenerative diseases.

It is another purpose of the present invention to provide a bigenic mouse that can be used to determine whether a compound causes or modulates some aspect of Alzheimer's, Frontal Temporal Dementia, Parkinson-like and other neurodegerative diseases.

Further, it is a purpose of the present invention to provide a mouse capable of producing human Tau protein, human Tau protein isoforms and/or mutated isoforms of the human Tau protein, which proteins can then be recovered for laboratory and therapeutic uses.

To achieve the forgoing and other purposes of the present invention there is provided a bigenic mouse whose germ cells and somatic cells contain (i) an inactive mouse TAU gene, and/or (ii) a transgene encoding the human TAU gene and/or mutated human TAU genes. This transgene includes the regulatory elements of the human TAU gene that are necessary for neuronal expression of said transgene in said bigenic mouse, and/or for human patterns of expression of said transgene in said bigenic mouse.

The bigenic mice of the invention may contain one or two alleles for the human TAU gene as a transgene in unknown number and/or location in the mouse genome (i.e., one or two TAU alleles) and two alleles of the disrupted mouse TAU gene (i.e., homozygous TAU knockout background or null background).

The bigenic mice are useful as a model of Alzheimer's disease and of Frontal Temporal Dementia's such as FTDP-17, Progressive Supra-Nuclear Palsy, Cortical Basal Degeneration and/or Pick's disease, and as a source of human TAU protein and/or human TAU protein isoforms and/or mutated isoforms of the human TAU protein.

Another aspect of the invention is the use of a bigenic mouse, as described above, to determine whether a compound modulates (e.g., induces, treats) some aspect of Alzheimer's disease and/or neurodegenerative disease that is displayed by the said bigenic animal, by administering said animal such compound, and then examining the animal for modulation of the disease characteristic, and/or changes in TAU expression and/or accumulation in said bigenic animal.

Also, the mice of the present invention may be used as a source of human Tau proteins, which may be collected from neuronal and/or glial cells of the mice, isolated in accordance with known techniques, and used, for among other things, to create laboratory reagents.

Other features and advantages of the present invention will be apparent from the following description taken in conjunction with the accompanying drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 1:
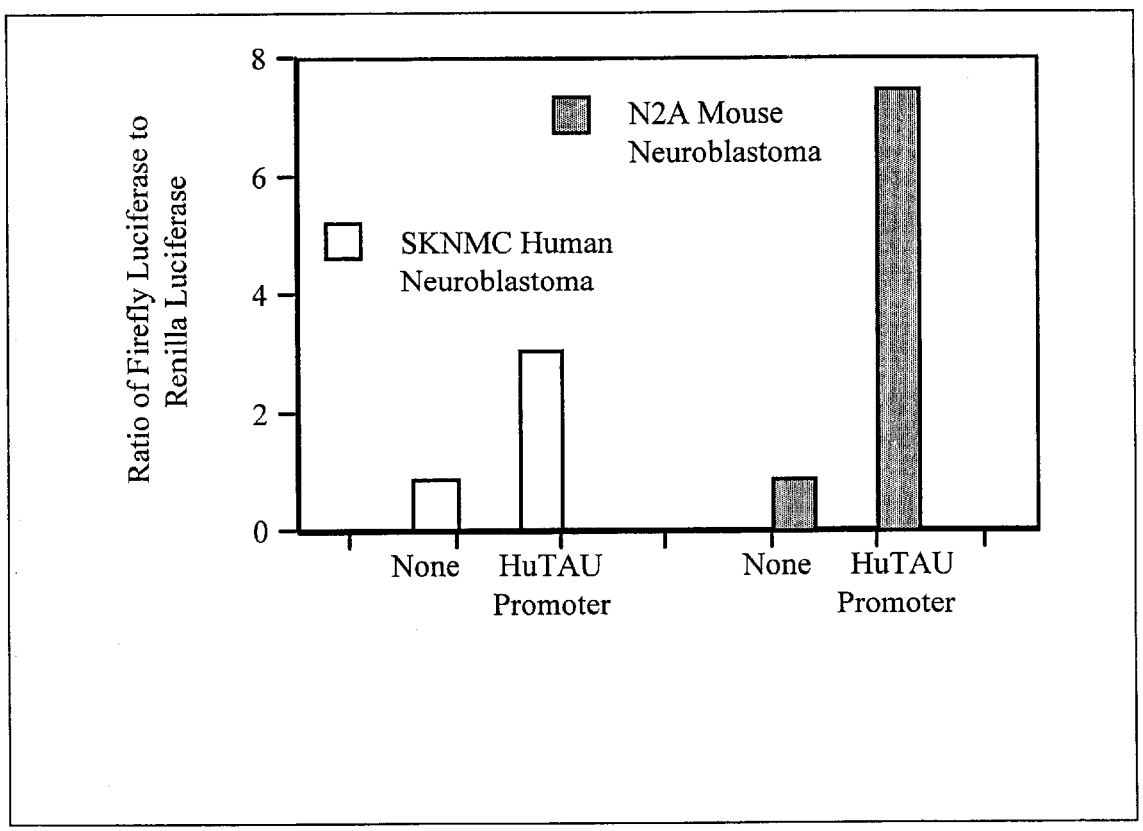
FIG. 1 is a graph showing the function of the human TAU promoter in mouse and human neuronal cells.

The human TAU gene is known and can be obtained in accordance with known techniques. See, e.g., Andreadis et al., *Biochemistry* 31,10626 (1992). In this regard, most of the sequences for the human TAU gene are included in Section II below. Nucleotide sequences are presented herein by single strand only, in the 5' to 3' direction and from left to right.

Mice containing an inactive or inactivated or disrupted mouse TAU gene (e.g., knockout mice) can be produced in accordance with the techniques described in Harada et al., *Nature* 369, 488 (1994). Particularly preferred mice for carrying out the present invention are also disclosed below. Such mice are useful as an intermediate for producing the bigenic mice described above.

The production of transgenic mice can be carried out in view of the disclosure provided herein and in light of techniques known to those skilled in the art, such as described in U.S. Pat. No. 5,767,337 to Roses et al.; U.S. Pat. No. 5,569,827 to Kessous-Elbaz et al.; and U.S. Pat. No. 5,569,824 to Donehower et al. (the disclosures of which are expressly incorporated by reference herein in their entirety).

Mice of the invention are preferably characterized by exhibiting expression of human TAU proteins in neuronal cells thereof, and/or a human pattern of human TAU protein expression in non-neuronal cells. By "human pattern" of expression is meant that the pattern of distribution of human TAU proteins is expressed in mouse neuronal cells, particularly in the axons thereof. Optionally, the human TAU protein may be expressed in the somatodendritic region of mouse neurons, and or form straight and/or paired helical filaments therein and/or produce neurofibrillary tangle pathology and/or neuropil thread pathology and/or neuronal loss therein and/or aggregates of intracellular proteins.

Thus, mice of the invention are useful for the study of the effects of different TAU protein isoforms (collectively referred to as human TAU proteins), and mutant protein isoforms of human TAU proteins (a.k.a. human TAU muteins) on brain biology, development, function, pathology, aging and/or injury.

Mice of the invention may be used as a source of human TAU proteins, which may be collected from neuronal and/or glial cells of the mice, isolated in accordance with known techniques, and used, among other things, as an immunogen to raise anti-TAU antibodies, which are in turn useful as laboratory reagents.

Mice of the invention as bigenic mice (with non-disrupted human TAU genes, i.e. wild-type human TAU genes) are useful as an animal model of Alzheimer's disease and other neurodegenerative diseases. Mice of the invention as bigenic mice (with mutated human TAU genes, i.e. mutated TAU genes) are also useful as an animal model of Alzheimer's disease and other neurodegenerative diseases.

The ability of a compound to induce Alzheimer's disease and/or induce Frontal Temporal Dementia (FTD) and/or some key characteristic of either disease may be determined or screened by administering a test compound to an animal of the invention and then monitoring the animal for the development of the disease (e.g., by monitoring for one or more sign, symptom or indicia of such a disease such as an underlying physiological event correlated to the presence of the disease).

Further, the ability of a compound to treat such diseases may be determined or screened by administering a test compound to an animal of the invention and then monitoring that animal for treatment of the disease (e.g., the alleviation, reduction, arresting or slowing of the progress of one or more sign, symptom or indicia of such a disease). Animals may be administered a test compound by any suitable means, such as by parenteral injection, oral administration, inhalation administration, transdermal administration, etc.

The invention comprises transgenic mice and bigenic mice. Transgenic mice are made as described below to contain a transgene of the entire human TAU gene and/or human TAU cDNA and/or a mutated human TAU cDNA. Bigenic mice are transgenic mice that, in the preferred embodiment, are repeatedly mated to "knockout" mice so that they only contain disrupted mouse TAU genes and a transgene of the entire human TAU gene and/or human TAU cDNA and/or a mutated human TAU cDNA.

Preferred "knockout" mice or "null" mice of the invention are mice whose germ and somatic cells contain an inactive mouse TAU gene or disrupted mouse TAU gene, wherein Exon 1 (or other suitable segment) of said mouse TAU gene is deleted and replaced with an expression cassette, said expression cassette including a heterologous gene (e.g., a gene encoding a marker such as a neomycin resistance gene) operably associated with a promoter (e.g., an inducible or constitutively active promoter such as a PGK promoter). Thus, the mouse TAU gene is "disrupted" by the presence of the heterologous gene. This disrupted TAU gene is then unable to program the expression of functional mouse Tau proteins.

The transgene inserted into animals of the invention (transgenic animals) is, in general, one that encodes a human TAU gene and/or a human TAU cDNA and/or its mutated analogs. The gene may be either a genomic sequence (that is, one that includes both introns and exons) or may be a cDNA encoding human TAU proteins and/or human TAU muteins. The gene may be any and/or all TAU isoforms, and may include one or more mutations to the sequence thereof particularly from among the known human TAU gene mutations and/or proprietary human TAU gene mutations.

Bigenic mice are created by mating TAU knockout mice to transgenic TAU mice where the transgene is the entire human TAU gene or human TAU cDNA or mutated human TAU cDNA. Exon 1 of the murine-TAU gene is removed to make TAU-knockout mice (muTAU-KO). The entire human TAU gene or human TAU cDNA or mutated human TAU cDNA is added to a mouse cell to make human-TAU transgenic mice (huTAU-Tg). These mice are mated to obtain a mouse that expresses only human Tau protein (huTAU-Tg/homozygous-muTAU-KO). These huTAU-Tg transgenic mice and/or huTAU-Tg/muTAU-KO bigenic mice are then examined for "Alzheimer's-like-Tau-pathologies" and/or "Frontal Temporal Dementia"(FTD) pathologies and/or "Frontal Temporal Dementia with Parkinsonism"(FTDP) pathologies. In addition to this genetic stress, these animals may be further stressed with aging and/or glyco-oxidation and/or fasting and/or mating to other transgenic mice and/or treatment with a compound and then their brain pathological and/or functional responses are measured. Other Alzheimer's disease characteristics, in addition to Alzheimer's-like Tau pathologies, including neuronal loss, oxidative stress markers, inflammation markers, gliosis, glial inclusions, neuronal inclusions, behavioral deficits and other cellular changes, are also screened in animals of the invention, particularly in characterizing the animals or where the animals are used to screen for compounds that modulate Alzheimer's and/or FTD and/or FTDP diseases.

I. EXAMPLES

The following examples are intended to provide those of ordinary skill in the art with a complete disclosure and description of how to manipulate the DNA sequences, and make the transgenic mammals and proteins of the invention and are not intended to limit the scope of what the inventors regard as their invention. Efforts have been made to ensure accuracy with respect to numbers used (e.g., amounts, temperature, etc.) but some experimental errors and deviation should be accounted for.

Example 1

Activity of the Human TAU Promoter in Mouse Neuronal Cells

The partial gene sequence of the human TAU gene promoter used in the present invention follows:
CTCGAGGGCCGGCCACGTGGAAGGC-
CGCTCAGGACTTCTGTAGGAGAGGACAC-
CGCCCCAGGCTGACTGAAAG-
TAAAGGGCAGCGGACCAGCGGCGGAGCCAC
TGGCCTTGCCGCATGGCCCGAAGGAGGA-
CACCCACCCCCGCAACGACACAAA-
GACTCCAACTACAGGAGGTG-
GAGAAAGCGCGTGCGCCACGGAAGCGCG
TGCGCGCGCGGTCAGCGCCGCGGCCT-
GAGGCGTAGCGGGAGGGGGACCGC-
GAAAGGGCAGCGCCGAGAGGAACGAGC-
CGGGAGACGCCGGACGGCCGAGCGGCAGG
GCGCTCGCGCGCCCACTAGTGGCCGGAG-
GAGAAGGCCCCGCGGAGGCCGCGCTGC-
CCGCCCCCTCCCCTGGGGAGGCTCGCGT-
TCCCGCTGCTCGCGCCTGCCGCCCGCCGGCC
TCAGGAACGCGCCCTCTCGC-
CGCGCGCGCCCTCGCAGTCACCGCCAC-
CCACCAGCTCCGGCACCAACAGCAGCGC-
CGCTGCCACCGCCCACCTTCTGCCGCCG
CCACCACAGCCACCTTCTCCTCCTC-
CGCTGTCCTCTCCCGTCCTCGCCTCT-
GTCGAGTATCAGGTGAACTTTGAACCAG-
GATGGCTGAGCCCCGCCAGGAGTTC
GAAGTGATGGAAGATCACGCTGGGACG-
TACGGGTTGGGGGACAGGAAAGAT-
CAGGGGGGCTACACCATGCACCAAGAC-
CAAGAGGGTGACACGGACGCTGGCCTGAAAG
(SEQ. ID NO: 1)

FIG. 1 shows that this human TAU promoter is active in mouse and in human neuronal cells. More particularly, transgenic mice were generated using the human TAU gene's promoter to drive expression of the human TAU gene, human TAU cDNAs and mutated TAU cDNAs in mouse brain. In order for this strategy to work, the human TAU promoter must be active in mouse cells and preferably, in mouse neuronal cells. The Promega firefly luciferase/renilla luciferase system has previously been employed to measure the activity of the Presenilin-1 promoter (Mitsuda et al. J. Biol. Chem. 272: 23489–97 (1997)). To test whether the human TAU promoter is active in mouse neuronal cells, this same system was employed.

About 5,000 base pairs of the region upstream from Exon-minus-1 of the human TAU gene (Sac I to Sal I DNA fragment) was cloned into the pGL3 vector so that the human TAU promoter's ability to stimulate firefly luciferase activity in these cells could be measured. The pGL3 vector that lacks a promoter, shown as "None" in FIG. 1, was co-transfected with a plasmid expressing renilla luciferase into the SKNMC human neuroblastoma cell line and into the N2A mouse neuroblastoma cell line using Lipofectin (BRL) and standard methods (Mitsuda et al. J. Biol. Chem. 272: 23489–97 (1997)). Constructs of the human TAU promoter in pGL3 were co-transfected into separate cultures of SKNMC and N2A cells by the same method as above. Cells were allowed to recover for 48 hours after transfection and assayed for both firefly luciferase and renilla luciferase using a Turner luminometer and instructions from Promega. The ratio of firefly luciferase activity to renilla luciferase activity was calculated for each culture and graphed. Compared to no promoter ("None"), the human TAU promoter ("HuTAU Promoter") was active in both human neuroblastoma cells and in mouse neuroblastoma cells. This result indicates that the human TAU promoter can function in mouse neurons in a transgenic mouse carrying the human TAU gene.

Examples 2–12

Making a TAU-Knockout Mouse (muTAU-KO) by Removing Exon-1 of the Murine TAU-gene and Confirming Lack of Expression A knockout mouse is created when a critical portion of a gene is removed and/or disrupted thereby preventing the altered gene from expressing its normal protein product. A growing literature is filled with examples of knockout mice including the report of Harada et al., Nature 369, 488–491 (1994) where the gene encoding mouse Tau protein was disrupted, resulting in a viable mouse that did not express Tau protein, but had fewer microtubules in its small caliber axons. This TAU-knockout mouse was generated by a process of homologous recombination between portions of the mouse TAU gene and a targeting vector containing mouse TAU genomic DNA placed on both sides of a PGK-neo gene (phosphoglyceraldehyde kinase promoter driving the bacterial neomycin resistance gene) which confers resistance to the neomycin analog, G418. Specifically, the targeting vector contained the herpes simplex virus thymidine kinase gene (HSV-TK), followed by about 2000 bp of the mouse TAU gene's intron between Exon-minus 1 and Exon 1, the PGK-neomycin resistance gene cassette, and about 4000 bp of the mouse genomic DNA from the intronic region downstream from Exon 1 and Exon 2 of the mouse TAU gene.

This targeting vector was transfected into mouse embryonic stem cells. Transfected cells were selected with G418 (a neomycin analog) for the presence of the PGK-neomycin resistance gene and with gangcyclovir for the absence of the HSV-thymidine kinase gene. This pattern of G418 resistance and gangcyclovir resistance occurs when homologous recombination has occurred between the targeting vector and the embryonic stem cell's genomic DNA (i.e. ES-genomic DNA). Specifically, two homologous recombination events occurred to generate this dual drug resistance phenotype. The first recombination was between the TAU gene's upstream intron region with the mouse embryonic stem cell's genomic DNA. The second recombination was between the TAU gene's downstream intronic region (between Exon 1 and Exon 2) and Exon 2 with the mouse embryonic stem cell's genomic DNA. In this case, the DNA encoding the PGK-neomycin resistance gene was introduced into the embryonic stem cell's genomic DNA in place of Exon 1 of the TAU gene and the thymidine kinase gene was not introduced into the genomic DNA. G418 resistant and gangcyclovir resistant cells were diluted to about one cell per well and colonies arising from single cell clones were expanded on feeder layers of mouse embryonic fibroblast cells. Genomic DNA from expanded clones was Southern blotted and probed for the presence of the PGK-neomycin resistance gene's DNA and lack of thymidine kinase gene's DNA by hybridization and/or polymerase chain reaction (PCR). Individual clones of cells, having the proper antibiotic resistance and hybridization patterns, were injected into mouse blastocysts which were then implanted into pseudopregant females. The resulting offspring are chimeras containing cells homozygous for the wild-type mouse TAU gene and heterozygous cells containing a wild-type mouse TAU gene on one allele, and a disrupted mouse TAU gene in which Exon 1 was replaced with the PGK-neomycin resistance gene on the other allele. The chimeric males are then mated to wild-type females and the DNA of the offspring genotyped for the presence of the PGK-neomycin-resistance gene. By "wild-type" mouse is meant a mouse that does not contain the human-TAU transgene, and does contain at least one active mouse TAU gene (e.g., one or two mouse TAU alleles).

In the alternative, chimeric females can be mated to wild-type males. The F1 offspring of these matings between chimeric mice with positive genotypes for the heterozygous presence of the PGK-neomycin-resistance gene (heterozygous muTAU-KO), are mated with one another to generate mice homozygous for the presence of the PGK-neomycin-resistance gene and homozygous for the absence of Exon 1 of the mouse TAU gene, that is, a "TAU-knockout" mouse (a.k.a. homozygous muTAU-KO).

Example 2

Mapping the Mouse-TAU Gene

A BAC clone "D" containing the mouse TAU gene's Exon-minus 1, Exon 1 and Exon 13, as defined by PCR, is isolated. Following an EcoR1 digest of the BAC clone "D" DNA and subcloning its fragments into the pBluescript II KS+ vector, one plasmid subclone pBS#1 is identified as containing Exon 1 of the mouse TAU gene by DNA sequence analysis and comparison to published mouse TAU gene's DNA sequences (Andreadis et al., *Biochemistry* 31, 10626 (1992)). DNA sequencing shows this subclone to contain about 5000 bp of the mouse TAU gene surrounding Exon 1. It was felt, however, that this subclone was too small to give a high percentage chance of success in a homologous recombination strategy. Thus, a larger piece of DNA corresponding to the intron downstream of Exon 1 and Exon 2 of the mouse TAU gene was subcloned. The exact restriction map for this region of the mouse TAU gene is not known. The map was made using Southern blots of mouse genomic DNA and of BAC clone "D" DNA cleaved with Not I, Xho I, Xba I, Bam H1, Asp 718 and Kpn I (these are unique sites available in the pPNT vector), probed with sequences specific for Exon-minus 1, Exon 1 and/or Exon 2, and a restriction enzyme map was generated. Each of these restriction enzyme fragments was subcloned into similarly cleaved pBluescript II KS+ so that, for example, Kpn I digested BAC clone DNA was ligated into Kpn I digested pBluescript II KS+ DNA. Following transformation into competent bacteria (cloning efficiency DH5 alpha strain of *E. coli*, BRL, Bethesda, Md.), oligonucleotide hybridization was used to screen for subclones from each restriction enzyme-specific library that contains Exon-minus 1, Exon 1 and/or the intron downstream of Exon I and Exon 2. Each positive subclone's DNA was restriction enzyme mapped and sequenced on an Applied BioSystems model 370A automated DNA sequencer using kits and protocols provided by the supplier (ABI, Foster City, Calif.). All of this information was used to assemble a fine structure map of the mouse TAU gene.

Example 3

Engineering the Targeting Vector and ES Cell Selection

Figure 2:
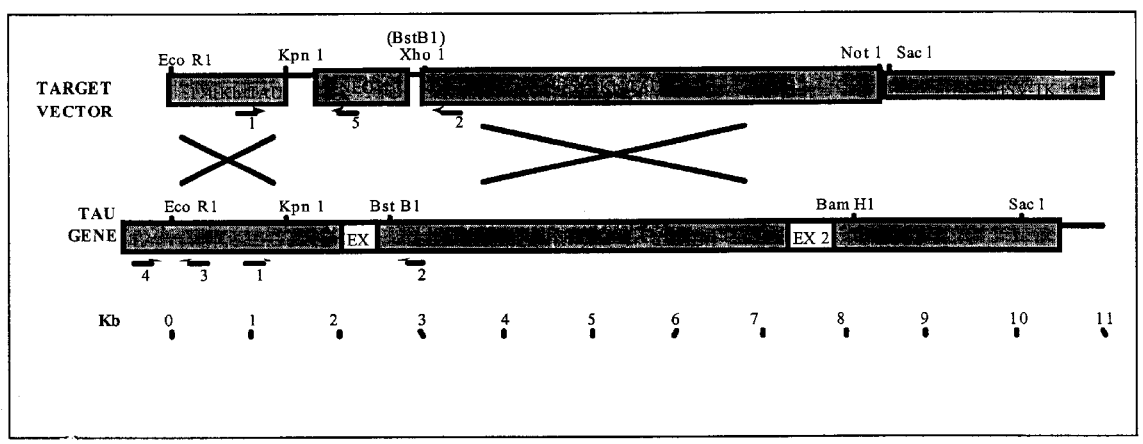
FIG. 2 is a map of the targeting vector used to disrupt Exon 1 of the mouse TAU gene.

A targeting vector was built to remove Exon 1 of the mouse TAU gene using about 1400 bp on the 5'-upstream side of Exon 1 (i.e. the intron DNA between Exon-minus 1 and Exon 1) and about 5500 bp on the 3'-downstream side of Exon 1 (i.e., the intron DNA downstream of Exon 1 and Exon 2) inserted into the pPNT vector (Tybulewicz et al., Cell 65, 1153 (1991)), as is shown in FIG. 2.

More particularly, FIG. 2 is a map of a portion of the targeting vector used to disrupt Exon 1 of the mouse TAU gene to generate a TAU knockout mouse. The restriction digest map surrounding Exon 1 and Exon 2 of the mouse TAU gene was determined by standard methods and the targeting vector was constructed for creating the TAU-knockout mouse. Utilizing the pPNT vector (Tybulewicz et al. Cell 65: 1153–1163 (1991)), a 1400 bp EcoRl-Kpn 1 mouse TAU gene fragment from the region 5' of Exon 1, was inserted into the Kpn 1 and EcoRl sites of pPNT which are on the 3' side of the NEO gene. A 5500 bp BstBl-BamHl mouse TAU gene fragment from the 3' side of Exon I (also encompassing Exon 2), was inserted into the Not 1 and Xho 1 sites of the pPNT vector which are on the 5' side of the NEO gene. Restriction analysis and sequencing confirmed the presence and position of the TAU gene's DNA fragments that were inserted into the pPNT vector.

It is preferable to have the neomycin resistance gene transcribed in the opposite direction of the TAU gene's normal direction of transcription so as to inhibit low levels of TAU gene transcription fortuitously occurring from the PGK promoter used to drive neomycin resistance gene (PGKneo) transcription. To do this, the 5'-upstream mouse TAU gene DNA is inserted on the 3' side of the neomycin resistance gene (PGKneo) and the 3'-downstream mouse TAU gene DNA is inserted on the 5' side (FIG. 2). The orientation of each insert is confirmed by automated DNA sequencing of the plasmid targeting vector which is called "pReplace TAU Exon 1 with PGKneo" (i.e. a pPNT plasmid with the following order of DNA sequences: mouse TAU gene's 3'-intron and then PGKneo gene and then mouse TAU gene's 5'-intron). Double-CsCl banded, Hind III linearized "pReplace TAU Exon 1 with PGKneo" vector DNA was sent to Genome Systems (St. Louis, Mo.) for electroporation into RW4 embryonic stem cells which are grown on feeder layers of mouse embryonic fibroblasts.

Those cells carrying the PGKneo gene and lacking the HSV-thymidine kinase gene are selected in G418 and gangcyclovir. At this stage, colonies arising from single cells are isolated with cloning cylinders, transferred to 24 well microtiter plates and grown to increase cell numbers. A portion of each of these clonal cell lines is frozen for later use and the remainder resuspended in 5 cell volumes of TBE (10 mM Tris-HCl, pH 7.4 and 1 mM EDTA, pH 7.4), extracted twice with 2 volumes of phenol:chloroform:isoamyl alcohol (50:48:2), re-extracted with 2 volumes of chloroform:isoamyl alcohol (24:1) and re-extracted with 2 volumes of ether. Residual ether in the aqueous phase is removed by drying under a stream of nitrogen gas.

Clonal cell DNA is analyzed by PCR for the presence of the PGKneo gene by observation of an appropriately sized PCR product and by the PCR-product's sequence matching a portion of the PGKneo DNA sequence. The presence of an Exon 13 specific PCR product whose sequence matches the mouse TAU gene sequence serves as a positive control for the PCR assay. Clonal cell DNA is also cut with restriction enzymes, Southern blotted and hybridized to PGKneo, Exon 1 and promoter-specific DNA probes labeled with 32P-dCTP via hexamer/random priming method.

If the targeted replacement has worked properly by homologous recombination, the Southerns hybridized with PGKneo probe will give one band, the Exon 1 probe gives another band (which should be the same as is found in genomic DNA from non-transfected ES cells), and the intron-specific probe (intron sequences between Exon 1 and Exon-2) gives two bands, one of which is the same as non-transfected ES cells' genomic DNA and the other being of different size because it contains the PGKneo sequence.

Example 4

Creating the Knockout Mice

Clonal cells containing the PGKneo gene and lacking the HSV-thymidine kinase gene by resistance to G4 18 and gangcyclovir, by PCR product analysis and by Southern blot hybridization, are expanded and prepared for blastocyst injection, by any suitable service provider (e.g., DNX, Inc.). Blastocysts are implanted into pseudopregant female mice and the service provider monitors the birth of the pups and maintains the chimeric mice ($F_0$ founders) in an approved animal facility. Chimeric agouti-coat color males are mated to wild type black female mice and tail snips of the offspring (F1 generation) are analyzed by PCR and Southern blot in accordance with standard techniques. Some of these F1 mice may be heterozygous because they contain the wild-type mouse TAU gene on one allele and the PGKneo gene in place of the mouse TAU-gene's Exon 1 on the other allele, i.e. (+/−) with respect to TAU-Exon 1 (agouti coat color should be an indicator of the presence of the PGKneo replacement). Genomic DNA is extracted from the tail snips with a proteinase-K digestion followed by high salt and/or phenol extraction in accordance with standard techniques. Both PCR and Southern blot hybridizations of this tail snip DNA are utilized to confirm the presence of PGKneo gene, the absence of the HSV-thymidine kinase gene and a change in size of the fragment carrying the intron between Exon 1 and Exon 2 of the mouse TAU gene.

A breeding pair of heterozygous TAU knockout mice (+/− with respect to mouse TAU Exon 1 so that the "+" allele represents the intact mouse TAU gene and the "−" allele represents the disrupted mouse TAU gene containing the PGKneo gene in place of Exon 1) are mated to give homozyous TAU knockout mice (−/−), heterozygous TAU knockout mice (+/−) and homozygous wild-type mice (+/+) with respect to Exon- 1 of the TAU gene. In general, a male mouse and a female mouse are placed together in a cage, allowed to mate, the male removed after a few days and the female allowed to birth her pups in about 3 weeks time. The pups then stay with their mother for about another 3 weeks until they are weaned, tail snips (about 5 mm of the end of the tail) are taken and tags bearing identification numbers attached to the ears. From this point, the mice are allowed to reach sexual maturity over the next 4 weeks while their tail snip DNA is genotyped. By PCR and Southern analysis, homozyous TAU knockout mice (−/− with respect to mouse TAU gene) are diagnosed by PCR analysis and Southern blot analysis if they lack Exon 1 of the TAU gene, contain the PGKneo gene, and display a change in size of the fragment carrying the intron between Exon 1 and Exon 2 of the mouse TAU gene.

Example 5

Characterizing Tau Expression

Once homozygous TAU knockout mice are identified, their brains are removed and analyzed for the presence of Tau mRNA and Tau protein. Total brain RNA is isolated (Ambion kit or TRIzol reagent, BRL), denatured and Northern blotted to nitrocellulose and the blots hybridized to 32P-labeled probes (see Vitek et al., *Molecular Brain Res.* 4: 121 (1988) for methods) specific for Exon 1 of mouse TAU and for full length mouse Tau cDNA (Lee et al. *Science* 239: 285 (1988)). As a positive control, Northerns are stripped and reprobed with an APP cDNA probe as described in Vitek et al. (1988). Western blots of total brain homogenates (see Sahasrabudhe et al., *J. Biol. Chem.* 267, 25602 (1992)) are stained with anti-Tau antibodies: AT8 (Innogenetics, N.V., Belgium), Tau-2 (Sigma, St. Louis, Mo.), Tau-14 (Calbiochem, San Diego, Calif.) and carboxy-terminal anti-Tau (Accurate, Farmingdale, N.Y.) (Kosik et al., *Neuron* 1, 817 (1988), Mercken et al., *Acta Neuropathol.* 84, 265 (1992)). As positive controls, anti-amyloid precursor protein antibodies (#22C11, Boehringer Mannheim, Indianapolis, Ind.) and 6E10 (Senetek, Maryland Heights, Mo.), are used with Western blots. In both Northern and Western blots, homozygous TAU knockout mice essentially lack hybridizable Tau mRNA and lack immunoreactive Tau protein. Wild-type mice contain Tau mRNA (bands of about 6 kB and 8 kB in size) and Tau protein (a series of closely spaced bands ranging anywhere from 45 to 68 kDa in size). Heterozygous TAU knockout mice may contain reduced levels of Tau RNA and Tau protein when compared to wild-type control mice.

Example 6

Alternative Methods for Yielding Knockout Mouse

There are several alternative technologies to the homologous recombination replacement method listed above that will also yield a TAU knockout mouse that lacks expression of Tau protein. For example, the Cre-lox method (Ramirez-Solis et al., *Nature* 378, 720 (1995)) which may be done under contract with Lexicon Genetics Inc. (Woodlands, Tex.), requires that small "lox" sequences be introduced on both sides of Exon 1 of the mouse TAU gene. These lox sequences are placed in those positions, for example, through two sequential homologous recombination procedures as outlined above. Once mice with the proper genomic pattern of lox sites are obtained as defined by DNA sequencing, they are mated to mice that express the bacteriophage site-specific recombinase, Cre. The Cre recombinase cleaves the genomic DNA at the "lox" sites and anastomoses the free ends together to remove the region between the lox sites from the genomic DNA, thus creating a deletion of Exon 1 in the genomic DNA encoding the mouse TAU gene. The advantage of this system is that the Cre recombinase can be expressed under a variety of promoters that are either specific for a certain type of cell, specific for a particular developmental stage or are specifically induced following treatment with a ligand such as in the tetracycline-inducible promoters (St. Onge et al., *Nucleic Acids Res.* 24, 3875 (1996)). The control provided by restricted Cre expression may be useful in future modeling of specific patterns of Tau protein expression.

Examples 7–11

Making a Human-TAU Transgenic Mouse (huTAU-Tg) by Insertion of the Human TAU Gene

Example 7

Cloning the Human-TAU Gene

The human TAU gene sequence is cloned with reference to the sequence reported by Andreadis et al., *Biochemistry* 31, 10626 (1992). Briefly, a forward oligonucleotide primer (Forward-Promoter Primer=5'-CCGCAACGACACAAAGACTCC-3' (SEQ ID NO: 2) and a reverse primer (Reverse Promoter Primer=5'-GAGGAGAAGGTGGCTGTGGTG-3' (SEQ ID NO: 3) from the promoter and from the 5'-untranslated region of the human TAU gene's sequence were chosen for PCR reactions. When used with human genomic DNA, these primers gave about a 400 bp PCR product whose sequence, obtained by DNA sequence analysis, matches that reported for the human TAU gene's promoter. When combined with mouse genomic DNA, these human-specific TAU promoter primers gave no PCR product with the size or sequence of those observed when used with the human TAU gene.

As a control, a human TAU gene Exon-14-specific forward primer (Exon-14 Forward Primer=TTGGCACTTCGATGATGACCTC (SEQ ID NO: 4) and reverse primer (Exon-14 Reverse Primer=CATTGTGACGTGTGATGAGGGG (SEQ ID NO: 5) gave a PCR product of 420 bp whose sequence matches that reported (Andreadis et al. 1992). Thus, these primers are specific for human DNA and for the human TAU gene.

The hexamer/random priming kit (Promega) and 32P-dCTP is used to label these human-specific PCR products to be used as probes to find clones of the human TAU gene. A human genomic DNA library in a PAC vector (Genome Systems) is probed by hybridization to these labeled probes (see Vitek et al. 1988). Positively hybridizing clones are identified on the gridded filter sets and all clones ordered from the company (Genome Systems).

Once PAC clones are identified by hybridization, then PCR is used with the promoter primer pair (above) or with the Exon-14 primer pair (above) and each PAC clone's DNA, to identify those clones containing the 5' promoter sequences and the 3'-Exon-14 sequences. Each clone that contains both the 5' and 3' ends of the human TAU gene, is subjected to additional PCR reactions with primers to each of the 15 Exons. Each of these Exon-specific PCR products is sequenced and compared to the reported sequences. A restriction map of each of these clones is made as described -above. Southern blots of the positive PAC clones and of human genomic DNA is hybridized with Exon-specific DNA probes as above. The PAC clone(s) containing all of the human Exons, with the correct DNA sequences and restriction maps matching human genomic DNA, were used to generate the "genomic human-TAU" transgenic mouse (huTAU-Tg).

Figure 3:
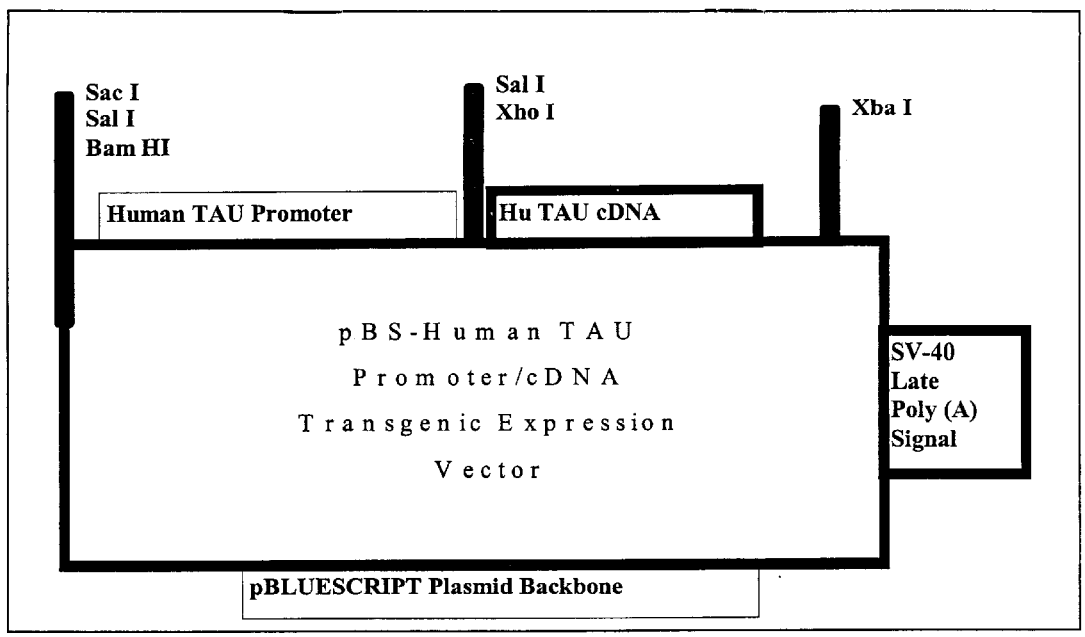
FIG. 3 is a map of the expression construct containing the human TAU gene's promoter and human TAU cDNA that was inserted into the mouse genome.

FIG. 3 is a map of the expression construct containing the human TAU gene's promoter and the human TAU cDNA that was inserted into the mouse genome to generate a human TAU cDNA transgenic mouse.

Initially, a Sac I to Sal I DNA fragment of about 5000 bp of the human TAU gene's promoter is cloned into the pBluescript II KS+ vector. Once the position of the promoter fragment was verified by DNA sequencing, a Kpn I to Xba I DNA fragment containing the entire cDNA encoding the "4-repeat" (i.e. 4 microtubule binding domains) of human Tau protein (Tau-441 cDNA) is cloned into the appropriate restriction enzyme sites in the promoter-containing vector. In some cases, the cDNA is mutated with a Promega Gene Editor kit to introduce mutations into the cDNA that encode the mutated Tau proteins like G272V, P301L, V337M, R406W and others that have been reported to be associated with Frontal Temporal Dementia diseases.

As detailed below, plasmid linearized by restriction enzyme digestion is purified and the DNA is then microinjected into mouse cells for generation of transgenic mice.

Example 8

Making the "Genomic Human-TAU" Transgenic Mouse

The entire human-TAU gene was used to generate the genomic human-TAU transgenic mouse (huTAU-Tg) by conventional methods (Roses et al. U.S. Pat. No. 5,767,337 and references therein). That is, DNA from the PAC clones, identified above to contain the entire human-TAU gene, is purified according to the instructions provided by DNX Inc., linearized with Not I (or another suitable rare cutter) and injected into the pronucleus of a fertilized mouse egg. Alternatively, circular, non-linearized DNA may be purified for microinjection into mouse cells. The injected eggs are re-implanted into pseudopregnant female mice that give birth to the pups. After about 3 weeks, when the pups are weaned, tail snips are taken and identification tags placed on each animal's ears. Genomic DNA is extracted from the tails of these founder mice (F0 generation) as described above. This DNA is genotyped for the presence of the human TAU gene using human-specific DNA probes from human TAU Exon-1 (ACGTACGGGTTGGGGGACAGGAAAGATCA GGGGGGC) (SEQ ID NO: 6) and from the 3'-untranslated region of the human TAU gene (Expressed Sequence Tag clone EST-27521 Genbank Accession # AA 324581) by Southern and by PCR analysis as described above.

The F0 mice containing the human TAU gene are mated to wild-type mice and their offspring (F1 generation) ear-tagged and genotyped for the presence of the human-TAU gene from the tail snip DNAs as described above. F1 mice carrying the human TAU gene have passed this gene through the germ-line.

Example 9

Identifying Homozygous Human-TAU Mice

To make huTAU-Tg mice homozygous for the presence of the human TAU transgene, F1 mice from a founder huTAU-Tg are mated via the procedure described above to generate offspring (F2 generation). About one fourth of these F2 mice are homozygous for the presence of the human TAU gene (as a randomly inserted transgene in unknown copy number), half are heterozygous for the human TAU gene and one fourth should lack the human TAU transgene.

The most reliable way to diagnose the presence of a homozygous human-TAU transgene in a homozygous murine-TAU background (i.e. in a wild-type mouse background) is to back-cross the putative homozygous human-TAU mice to wild-type mice and to genotype each of their offspring for the presence or absence of the human TAU gene. If the transgenic parent mouse was homozygous for the human TAU transgene, then after mating to a wild-type partner, each of the offspring should be heterozygous for the presence of the human TAU transgene. If the transgenic parent mouse was heterozygous for the human TAU transgene, then after mating to a wild-type partner, half of the offspring should be heterozygous for the presence of the human TAU transgene and the other half of the offspring should lack the transgene (i.e. will be wild-type). Putative homozygous TAU transgenic mice are mated twice to wild type partners and the offspring of each mating should all be heterozygous for the presence of the human TAU transgene in order to confirm that the parent was indeed homozygous for the human TAU transgene (homo-huTAU-Tg).

To perform the necessary genotyping, tail snip genomic DNA is extracted and subjected to PCR and/or Southern blot analysis for the presence of the human TAU transgene. For Southern analysis, EcoR1 digestion is favored because Exon 1 of the mouse TAU gene is carried on a 5 kBp EcoRI-EcoRI fragment and Exon 1 of the human TAU gene is carried on a 14 kBp EcoRI-EcoRI fragment (Andreadis et al. 1992). Southern blots of tail snip DNA are hybridized to a human TAU Exon 1 probe and to a mouse TAU Exon 1 probe. In this example, the genomic DNA fragment hybridizing to the human TAU probe (14 kBp) differs in length from the fragment hybridizing to the mouse TAU probe (5 kBp). Wild-type mice in this example should have a "human-TAU signal" of zero, as the probe is specific for the human-TAU gene DNA that they lack. Conversely, heterozygous huTAU-Tg mice and homozygous huTAU-Tg mice should display a human-TAU hybridization signal at 14 kBp. Heterozygous huTAU-Tg mice display a human-TAU hybridization signal at 14 kBp and a mouse-TAU hybridization signal at 5 kBp.

Example 10

Characterizing Human-Tau RNA and Human-Tau Protein Expression

Successful expression of human Tau protein is one goal of these efforts. Human TAU transgene expression is assessed at the RNA and at the protein levels. To measure human Tau-mRNA, RNA is extracted from the brain, is denatured by any of a variety of standard protocols, separated by size on agarose gels and blotted to a solid support like nitrocellulose to generate a "Northern" blot. When Tau mRNA is present in the sample, it hybridizes to the human-specific TAU probe (EST-27521) and stains RNA bands of about 6 kB and 2 kB in size as reported by Goedert et al., *Proc. Natl. Acad. Sci. USA* 85,4051 (1988). Although mouse Tau mRNA has been reported to run at 6 kB and 8 kB (Drubin et al., *J Cell Biol.* 98, 1090 (1984)), it should not cross-hybridize to the human probe which is specific for the human-TAU nucleotide sequence. As a positive control for hybridization, Northern blots are separately probed with an Amyloid Peptide Precursor cDNA probe (APP cDNA) for RNA bands in the 3 kB range (Vitek et al., U.S. Pat. No. 5,703,209). If the human-TAU transgene is being transcribed and post-transcriptionally spliced in mice, in a manner similar to that found in human brain, then animals homozygous and heterozygous for the human-TAU transgene should express RNA transcripts that hybridize to the human-specific TAU probe while wild-type mice, lacking the transgene, will not display hybridizing transcripts. Alternatively, the presence of Tau mRNA transcripts can be diagnosed with Reverse Transcriptase Polymerase Chain Reaction (RT-PCR) using brain RNA, extracted as described above, and an RT-PCR kit (BRL or Stratagene) to generate first strand complementary DNA (cDNA) followed by PCR with primers specific for the human Tau mRNA sequence and/or primers specific for Tau mRNA sequences.

Human Tau protein in brains of the various transgenic mice are measured by different methods. In the first method, brain (one hemisphere) of a mouse is homogenized in 25 mM Tris-HCl (pH 7.5), 3 mM MgCl2, 100 mM NaCl and 1 mM phenylmethylsulfonyl fluoride PMSF. In the second method, microtubules are prepared from brain homogenates and then Tau protein is prepared from those microtubule preparations by heat treatment and perchlorate treatment as described by Wilson and Binder, *J Biol. Chem.* 270, 24306 (1995). Protein concentrations are determined by Bradford and/or Lowry procedures following instructions from the manufacturer (Pierce). Proteins in the homogenate are mixed with an equal volume of 2×Laemmli sample buffer and boiled for 5 minutes. The proteins are resolved on 5 to 20% gradient gels (Novex), transferred to nitrocellulose membranes (BA85 or BA83, Schleicher and Schuell) and the "Western" blot is blocked in phosphate buffered saline containing 5% non-fat dried milk (weight per volume, "PBS/milk") to eliminate non-specific background staining. The anti-Tau monoclonal antibody, Tau-14, which recognizes human-Tau proteins and not mouse-Tau proteins according to the supplier (Calbiochem, see also Kosik et al., *Neuron* 1, 817 (1988)), is added at 1:500 dilution and incubated overnight at 4 degrees C. on a rocking platform. Blots are washed 3×10 minutes in PBS/milk and an appropriate secondary antibody linked to horse-radish peroxidase added at 1:5000 dilution for 2 hours at room temperature. Blots are washed 5×5 minutes in PBS and immunoreactivity visualized with an enhanced chemiluminescence detection kit (ECL, Amersham) and exposure to X-ray film. Similarly, additional Western blots of animals having and lacking the human-TAU transgene are probed with the anti-Tau antibodies: Alz50 (Davies), AT8 (Innogenetics), Tau-2 (Sigma) and the anti-C-terminal antibody (Accurate) for the presence of a tightly grouped set of protein bands in the 45 to 68 kDa range for human Tau proteins.

Mice lacking the mouse-TAU gene should also lack an immunoreactive set of Tau protein bands. In contrast, the huTAU-Tg and/or huTAU-Tg/muTAU-KO transgenic should express human Tau proteins, in all of the isoforms typically seen in human brain (Gotz et al., *EMBO J* 14: 1304 (1995), Bramblett et al., *Lab Invest.* 66: 212 (1992)). Some of the human Tau protein that is expressed in transgenic mice is abnormally phosphorylated (Gotz et al. 1995) and/or associated with paired helical filaments which may permit some antibodies like Alz50 and AT8 to react with a protein band of about 68 kDa in the human TAU transgenics, but not in the wild-type mice or knockout mice (see also Gotz et al. 1995). Again, a positive control for the Western blot technique is to stain blots with 22C11 and/or 6E10, anti-Amyloid Peptide Precursor antibodies which should react with a family of bands in the 110 to 130 kDa range.

Following observation of immunoreactive human Tau protein by Western blot analysis, human Tau protein expression is also localized by immunocytochemistry on brain slices from animals with and without the human TAU transgene. Homozygous muTAU-KO brains are used as a control for the specificity of the anti-Tau-protein antibodies. The methods used are well known (Lippa et al. *Neurology* 48, 515 (1997), Xu et al., *Neurobiol. Disease* 3, 229 (1996), Schmechel et al., *Proc. Natl. Acad. Sci. USA* 90, 9649 (1993)).

Briefly, brains from animals are removed and immersed in freshly prepared 4% paraformaldehyde in phosphate buffer (pH 7.4 to 7.6) for 1 to 2 days and then transferred to phosphate buffered saline (PBS) with a slight trace of formaldehyde for longer term storage. Fixed tissue is serially sectioned on an Oxford vibratome at 35–45 micrometers and reacted as free-floating sections for histological staining with Thioflavin-S (Dickson et al., *Neurobiol. Aging* 17, 733 (1996)). Thinner sections of about 10 micrometers or 20 micrometers are cut for immunocytochemistry using the avidin-biotin-peroxidase complex (ABC) methods using standard kits (Vector Labs, Burlingame, Calif.) and reacted with the Alz5O, AT8, Tau 2, Tau-14 and anti-carboxy-terminal tau antibodies (Kosik et al. *Neuron* 1, 817 (1988)) overnight at 4 degrees C. Sections are rinsed and reacted with appropriate secondary antibody conjugates and developed with diaminobenzidine as detection chromogen for peroxidase localization. Controls include staining with secondary antibody conjugates alone and ABC complex alone. Additional controls for the specificity of anti-Tau-protein staining are performed on muTAU-KO mice that lack the mouse-Tau-protein and its epitopes. In general, 15 minutes of 10% methanol/3% hydrogen peroxide pretreatment is employed to decrease endogenous peroxidase activity since the majority of tissues is fixed for a short time. Immunocytochemical staining of semi-adjacent sections is evaluated for Tau-protein-epitopes, phosphorylated-Tau-protein-epitopes, somatodendritic redistribution of Tau-protein-epitopes, neurofibrillary tangles, neuropil threads, dystrophic neurites and cellular staining with light microscopy of sections. Electron microscopy of brain tissue is performed after fixation of 3 to 5 mm slabs of brain that have been immersion fixed in 2% paraformaldehyde/2% glutaraldehyde in phosphate buffer (pH 7.4) for 24 hours. Fixed slabs are cut into 40 micrometer slices with a vibratome, stained with immunocytochemistry as detailed above, flat embedded in Epon, cut into silver to gold colored semi-thin sections, counter stained with uranyl acetate, collected on grids and viewed with any one of a variety of transmission electron microscopes.

Example 11

Alternative Methods for Making Human-TAU Transgenic Mouse

A cDNA that encodes one of the human Tau protein isoforms and/or a mutated Tau protein isoform can be expressed in transgenic animals (FIG. 3). In these cases, the expression of the TAU cDNA is driven by the human TAU gene's promoter (about 5000 bp as detailed above) and/or with a heterologous promoter such as Thy-1, that has been reported by Gotz et al. (1995) and/or other relevant promoters. Although the expression of just one isoform of human Tau protein may not generate the spectrum of at least 6 different Tau protein products, it will help to answer the question of whether the expression of human Tau protein, in the absence of all mouse Tau proteins (provided by the homozygous muTAU-KO animals), could predispose these bigenic animals toward hyperphosphorylation and/or somatodendritic redistribution of Tau protein and/or PHF and/or NFT formation and/or cell death. In particular, this approach has permitted the generation of transgenic animals carrying one or more mutations in the TAU gene that have been associated with the FTD-like diseases (Kwon et al., supra, at the Alzheimer Research Forum web page, Feb. 9, 2000, and references within). These mutations are introduced into the cDNA sequence using site-directed mutagenesis with synthetic oligonucleotides and a "matchmaker" site-directed mutagenesis kit according to instructions provided by the manufacturer.

Each mutated DNA is sequenced to confirm the presence of the mutated DNA sequence in S each clone. Once mutations have been confirmed, the DNA is linearized with a unique restriction enzyme that cleaves within the DNA sequences of the plasmid vector. Linearized DNA is then purified and microinjected into mouse cells as described above. Using this method, mutant DNAs encoding missense mutations in the protein and/or nonsense mutations in the protein and/or truncated forms of the protein and/or internal deletions in the protein may be expressed in transgenic mice and/or a wide variety of protein expression systems.

Example 12

Making a Mouse Expressing Only Human Tau Protein by Mating the Human-TAU Transgenic to the Murine-TAU-knockout (huTAU-Tg/homozygous-muTAU-KO)

After having generated transgenic and knockout mice as described above, an animal that has the human-TAU gene and/or TAU cDNA on a background that lacks a functional mouse-TAU gene is produced. In general, the mouse-TAU gene and human-TAU transgenes (TAU gene or TAU cDNA) are not linked, each segregates independently and each is inherited in a Mendelian fashion. In the first mating, a homozygous mouse-TAU knockout parent (homozygous-muTAU-KO) is mated to a homozygous human-TAU transgenic parent (that is also wild-type with respect to the mouse TAU gene, "homozygous-huTAU-Tg") to yield F1 offspring mice that are all heterozygous for the mouse-TAU gene and heterozygous for the human-TAU transgene (mu-TAU knockout/mu-TAU wild type at one locus and hu-TAU transgene on one allele at a different locus). Crossing these F1 mice to homozygous muTAU-KO mice yields F2 progeny where half the animals are homozygous muTAU-KO mice and the other half are heterozygous muTAU-KO mice. Of the F2 progeny that are homozygous for the muTAU-KO, half of these (or one fourth of all of the F2 progeny) will carry it the human TAU transgene and these desired mice are designated as huTAU-Tg/homozygous 1:5 muTAU-KO mice. These huTAU-Tg/homozygous muTAU-KO animals only express human Tau RNAs and human Tau proteins as shown using the methods described above.

II. Human Tau Gene Sequences

LOCUS NM_005910 2796 bp mRNA PRI 22-JAN-2000
DEFINITION *Homo sapiens* microtubule-associated protein tau (MAPT), mRNA.
ACCESSION NM_005910
VERSION NM_005910.2 GI:6754637
SOURCE human.
  ORGANISM *Homo sapiens*
    Eukaryota; Metazoa, Chordata; Craniata; Vertebrata; Mammalia; Eutheria; Primates; Catarrbini; Hominidae; Homo.
REFERENCE 1 (bases 1 to 2796)
  AUTHORS Goedert M. Wischik C M, Crowther R A, Walker J E and Klug A.
  TITLE Cloning and sequencing of the cDNA encoding a core protein of the paired helical filament of Alzheimer disease: identification as the microtubule-associated protein tau
  JOURNAL Proc. Natl. Acad. Sci. U.S.A. 85 (11), 4051–4055 (1988)
  MEDLINE 88234557
  PUBMED 3131773
REFERENCE 2 (bases 1 to 2796)
  AUTHORS Andreadis, A., Brown, W. M. and Kosik, K. S.
  TITLE Structure and novel exons of the human tau gene
  JOURNAL Biochemistry 31 (43), 10626–10633 (1992)
  MEDLINE 93041757
REFERENCE 3 (bases 1 to 2796)
  AUTHORS Lynch T, Sano M, Marder K S, Bell K L, Foster N L, Defendini R F, Sima A A, Keohane C, Nygaard T G, Fahn S and et al.
  TITLE Clinical characteristics of a family with chromosome 17-linked disinhibition-dementia-parkinsonism-amyotrophy complex
  JOURNAL Neurology 44 (10), 1878–1884 (1994)
  MEDLINE 95022204
  PUBMED 7936241
COMMENT REFSEQ: This reference sequence was derived from AF047863.1. On Jan 26, 2000 this sequence version replaced gi:5174526. PROVISIONAL RefSeq: This is a provisional reference sequence record that has not yet been subject to human review. The final curated reference sequence record may be somewhat different from this one.

| FEATURES | Location/Qualifiers |
|---|---|
| source | 1 . . . 2796 |
| | /organism="*Homo sapiens*" |
| | /db_xref="taxon:9606" |
| | /chromosome="17" |
| | /map="17q21.1" |
| | /cell_type="white blood cell" |
| | /dev_stage="adult" |
| gene | 1 . . . 2796 |
| | /gene="MAPT" |
| | /note="DDPAC; MSTD; MTBT1; FTDP-17" |
| | /db_xref="LocusID:4137" |
| | /db_xref"MIM:157140" |

| FEATURES | Location/Qualifiers |
|---|---|
| CDS | 237 ... 1562<br>/gene="MAPT"<br>/codon_start=1<br>/product="microtubule-associated protein tau"<br>/protein_id="NP_005901.2"<br>/db_xref="GI:6754638" |

/translation=
"MAEPRQEFEMEDHAGTYGLGDRKDQG-
GYTMHQDQEGDTDAGLKESPLQTPTEDG-
SEEPGSETSDAKSTPTAEDVTAPLVDEGAPGKQ
AAAQPHTEIPEGTTAEEAGIGDTPSLE-
DEAAGHVTQARMVSKSKDGTGSDDKKAK-
GADGKTKIATPRGAAPPGQKGQANATRI-
PAKTPPAPKTPPSSGEPPKSGDRSGYSSPOSPGTP
GSRSRTPSLPTPPTREPKKVAVVRTPPK-
SPSSAKSRLQTAPVPMPDLKNVKSKIG-
STENLKHQPGGGVQIINKKLDLSN-
VQSKCGSKDNIKHVPGGGSVQIVYKPVDLSKVT
SKCGSLGNIHHKPGGGQVEVKSEKLD-
FKDRVQSKIGSLDNITHVPGGGNKKI-
ETHKLTFRENAKAKTDHGAEIVYKSPV-
VSGDTSPRHLSNVSSTGSIDMVDSPQLATLAD
EVSASLAKQGL"
BASE COUNT 651 a 828 c 811 g 506 t
ORIGIN
1 CCTCCCCTGG GGAGGCTCGC GTRCCCGCTG
 CTCGCGCCTG CCGCCCGCCG OCCTCAGGAA
61 CGCGCCCTCT CGCCGCGCGC GCCCTCGCAG
 TCACCGCCAC CCACCAOCTC CGGCACCAAC
121 AGCAGCGCCG CTGCCACCGC CCACCTTCTG
 CCGCCGCCAC CACAGCCACC TTCTCCTCCT
181 CCGCTGTCCT CTCCGTCCT CGCCTCTGTC
 GACTATCAGG TGAACTGA ACCAGGATGC
241 CTGAGCCCCG CCAGGAGTTC GAAGTGATGG
 AAGATCACGC TGGGACGTAC GGGTTGGGGG
301 ACAGGAAAGA TCAGGGGGGC TACACCATGC
 ACCAAGACCA AGAGGGTGAC ACGGACGCTG
3361 GCCTGAAAGA ATCTCCCTG CAGACCCCCA
 CTGAGGACGG ATCTGAGGAA CCGGGCTCTG
421 AAACCTCTGA TGCTAAGAGC ACTCCAACAG
 CGGAAGATGT GACAGCACCC TTAGTGGATG
481 AGGGAGCC CGGCAAGCAG GCTGCCGCGC AGC-
 CCCACAC GGAGATCCCA GAAGGAACCA
541 CAGCTGAAGA AGCAGGCAT GGAGACACCC
 CCAGCCTGGA AGACGAAGCT GCTGGTCACG
601 TGACCCAAGC TCGCATGGTC AGTAAAAGCA
 AAGACGGAC TGGAAGCGAT GACAAAAAAG
661 CCAAGGGGGC TGATGGTAAA ACGAAGATCG
 CCACACCGCG GGGAGCAGCC CCTCCAGGCC
721 AGAAGGGCCA GGCCAACGCC ACCAGGATrC
 CAGCAAAAAC CcCGCCCGCT CCAAAGACAC
781 CACCCAGCTC TGGTGAACT CCAAAATCAG
 GGGATCGCAG CGGCTACAGC AGCCCCGCT
841 CCCCAGGCAC TCCCGGCAGC CGCTCCCGCA
 CCCCGTCCCT TCCAACCCCA CCCACCCGGG
901 AGCCCAAGAA GGTGGCAGTG GTCCGTACTC
 CACCCAAGTC GCCGTCTTCC GCCAAGAGCC
961 GCCTGCAGAC AGCCCCCGTG CCCATGCCAG
 ACCTGAAGAA TGTCAAGTCC AAGATCGGCT
1021 CCACTGAGAA CCTGAAGCAC CAGCCGGGAG
 GCGGGAAGGT GCAGATAATR AATAAGAAGC
1081 TGGATCTTAG CAACGTCCAG TCCAAGTGTG
 GCTCAAAGGA TAATATCAAA CACGTCCCGG 1141 AGGCGGCAG TGTGCAAATA GTCTACAAAC
 CAGTTGACCT GAGCAAGGTG ACCTCCAAGT
1201 GTGGCTCAT AGGCAACATC CATCATAAAC
 CAGGAGGTGG CCAGGTGAA GTAAAATCTG
1261 AGAAGCTTGA CTTCAAGGAC AGAGTCCAGT
 CGGATTGG GTCCACGGAC AATATCACCC
1321 ACGTCCCTGG CGGAGGAAAT AAAAAGATTG
 AAACCCACAA GCTGACCTTC CGCGAGAACG
1381 CCAAAGCCAA GACAGACCAC GGGGCGGAGA
 TCGTGTACAA GTCGCCAGTG GTGTCTG
1441 ACACGTCTCC ACGGCATCTC AGCAATGTCT
 CCTCCACCGG CAGCATCGAC ATGGTAGACT
1501 CGCCCCAGCT CGCCACGCA GCTGACGAGG
 TGTCTGCCTC CCTGCCAAG CAGGGTGT
1561 GATCAGGCCC CTGGGGCGGT CAATAATrGT
 GGAGAGGAGA GAATGAGAGA GTGTGGAAAA
1621 AAAAAGAATA ATGACCCGGC CCCCGCCCTC
 TGCCCCCAGC TGCTCCTCGC AGTTCGGTRA
1681 ATTGGTTAAT CACTAAC GCTGTCA CTCGGCIG
 GCTCGOGACT TCAAAATCAG
1741 TGATGGGAGT AAGAGCAAAT TTCATCTTTC
 CAAATTCGATG TGGCTAG TAATAAAATA
1801 TTTAAAAAAA AACATTCAAA AACATGGCCA
 CATCCAACAT TRCCTCAGGC AATTCCTTT
1861 GATTCTTTT TCTTCCCCCT CCATGTAGAA
 GAGGGAGAAG GAGAGGCT GAAAGGCT
1921 TCTGGGGGAT TTCAAGGGAC TGGGGGTGCC
 AACCACCTCT GGCCCTGTTG TGGGGGTTGT
1981 CACAGAGGCA GTGGCAGCAA CAAAGGATT
 GAAAACTTTG GTGTGTTCGT GGAGCCACAG
2041 GCAGACGATG TCAACCTTGT GTGAGTGTGA
 CGGGGGTGG GGTGGGGCGG GAGGCCACGG
2101 GGGAGGCCGA GGCAGGGGCT GGGCAGAGGG
 GAGGAGGAAG CACAAGAAGT GGGAGTGGGA
2161 GAGGAAGCCA CGTGCTGGAG AGTAGACATC
 CCCCTCCTTG CCGCTGGGAG AGCCAAGGCC
2221 TATGCCACCT GCAGCGTCTG AGCGGCCGCC
 TGTCCTTGGT GCCCGGGGGT GOGGGCCTGC
2281 TGTGGGTCAG TGTGCCACCC TCTGCAGGGC
 AGCCTGTGGG AGAAGGGACA GCGGGITAAA
2341 AAGAGAAGGC AAGCCTGGCA GGAGGGTTGG
 CACTTCGATG ATGACCTCCT TAGAAAGACT
2401 GACCTTGATG TCTTGAGAGC GCTGGCCTCT
 TCCTCCCTCC CTGCAGGGTA GGGCGCCTGA
2461 GCCTAGGCGG TTCCCTCTGC TCCACAGAAA
 CCCGTGYTTTA TTGAGTRCTG AAGGTTGGAA
2521 CTGCTGCCAT GATTTTGGCC ACTTTGCAGA
 CCTGGGACTT TAGGGCTAAC CAGTTCTCTT
2581 TGTAAGGACR TGTGCCTCTT GGGAGACGTC
 CACCCGTTTC CAAGCCTGGG CCACTGGCAT
2641 CTCTGGAGTG TGTGGGGGTC TGGGAGGCAG
 GTCCCGAGCC CCCTGTCCT CCCACGGCCA
2701 CTGCAGTCAC CCCGTCTGCG CCGCTGTGCT
 GTTGTCTGCC GTGAGAGCCC AATCACTGCC
2761 TATACCCCTC ATCACACGTC ACAATGTCCC
 GAATTC (SEQ ID NO: 7)
LOCUS HSAPTAU01 792 bp DNA PRI 25-FEB-1998
DEFINITION Homo sapiens microtubule-associated protein tau (tau) gene, exon 0.
ACCESSION AF047855 LA7238
1 VERSION AF047855.1 GI:2898163
SEGMENT 1 of 15
SOURCE human
 ORGANISM *Homo sapiens*
  Eukaryota; Metazoa; Chordata; Craniata; Vertebrata; Mammalia;
  Eutheria; Primates; Catarrhini; Hominidae; Homo.

REFERENCE 1 (bases 1 to 792)
  AUTHORS Andreadis, A., Brown, W. M. and Kosik, K. S.
  TITLE Structure and novel exons of the human tau gene
  JOURNAL Biochemistry 31 (43), 10626–10633 (1992)
  MEDLINE 93041757
REFERENCE 2 (bases 1 to 792)
  AUTHORS Andreadis, A., Wagner, B. K., Broderick, J. A. and Kosik, K. S.
  TITLE A tau promoter region without neuronal specificity
  JOURNAL J. Neurochem. 66 (6), 2257–2263 (1996)
  MEDLINE 96217356
REFERENCE 3 (bases 1 to 792)
  AUTHORS Andreadis, A.
  TITLE Direct Submission
  JOURNAL Submitted (13-FEB-1998) Biomedical Sciences, Shriver Center, 200 Trapelo Road, Waltham, Mass. 02154, USA
COMMENT On Feb. 24, 1998 this sequence version replaced gi: 1369994.

| FEATURES | Location/Qualifiers |
|---|---|
| source | 1 ... 792 |
| | /organism="Homo sapiens" |
| | /db_xref="taxon:9606" |
| | /chromosome="17" |
| | /map=17q21" |
| | /cell_type="white blood cell" |
| | /dev_stage="adult" |
| exon | 379 ... 597 |
| | /gene="tau" |
| | /note="designated as exon −1 in the literature" |
| | /number=0 |

BASE COUNT 120 a 323 c 261 g 88 t
ORIGIN
1 CTCGAGGGCC GGCCACGTGG AAGGCCGCTC AGGACTTCTG TAGGAGAGGA CACCGCCCCA
61 GGCTGACTGA AAGTAAAGGG CAGCGGACCA GCGGCGGAGC CACTGGCCTT GCCCCGACCC
121 CGCATGGCCC GAAGGAGGAC ACCCACCCCC GCAACGACAC AAAGACTCCA ACTACAGGAG
181 GTGGAGAAAG CGCGTGCGCC ACGGAAGCGC GTGCGCGCGC GGTCAGCGCC GCGGCCTGAG
241 GCGTAGCGGG AGGGGGACCG CGAAAGGGCA GCGCCGAGAG GAACGAGCCG GGAGACGCCG
301 GACGGCCGAG CGGCAGGGCG CTCGCGCGCC CACTAGTGGC CGGAGGAGAA GGCCCCGCGG
361 AGGCCGCGCT GCCCGCCCCC TCCCCTGGOG AGGCTCGCGT TCCCGCTGCT CGCGCCTGCC
421 GCCCGCCGGC CTCAGGAACG CGCCCTCTCG CCGCGCGCGC CCTCGCAGTC ACCGCCACCC
481 ACCAGCTCCG GCACCAACAG CAGCGCCGCT GCCACCGCCC ACCTTCTGCC GCCGCCACCA
541 CAGCCACCTT CTCCTCCTCC GCTGTCCTCT CCCGTCCTCG CCTCTGTCGA CTATCAGGTA
601 AGCGCCGCGG CTCCGAAATC TGCCTCGCCG TCCGCCTCTG TGCACCCCTG CGCCGCCGCC
661 CCTCGCCCTC CCTCTCCGCA GACTOGGGCT TCGTGCGCCG GGCATCGGTC GGGGCCACCG
721 CAGGGCCCCT CCCTGCCTCC CCTGCTCGGG GGCTGGGGCC AGGGCGGCCT GGAAAGGGCA
781 CCTGAGCAAG GG (SEQ ID NO: 8)
LOCUS HSAPTAU02 259 bp DNA PRI 25-FE3–1998
DEFINITION Homo sapiens microtubule-associated protein tau (tau) gene, exon 1.
ACCESSION AF027491
VERSION AF027491.1 GI:2598171
SEGMENT 2 of 15
SOURCE human
  ORGANISM Homo sapiens
    Eukaryota; Metazoa; Chordata; Craniata; Vertebrata; Mammalia; Eutheria; Primates; Catarrhini; Rominidae; Homo.
REFERENCE 1 (bases 1 to 259)
  AUTHORS Andreadis, A., Brown, W. M. and Kosik, K. S.
  TITLE Structure and novel exons of the human tau gene
  JOURNAL Biochemistry 31 (43), 10626–10633 (1992)
  MEDLINE 93041757
REFERENCE 2 (bases 1 to 259)
  AUTHORS Andreadis, A.
  TITLE Direct Submission
  JOURNAL Submitted (13-FEB-1998) Biomedical Sciences, Shriver Center, 200 Trapelo Road, Watham, Mass. 02154, USA

| FEATURES | Location/Qualifiers |
|---|---|
| source | 1 ... 259 |
| | /organism="Homo sapiens" |
| | /db_xref="taxon:9606" |
| | /chromosome="17" |
| | /map="17q21" |
| | /cell_type="white blood cell" |
| | /dev_stage="adult" |
| 5'UTR | join(AF047855.I:379 ... 597,72 ... 88) |
| | /gene="tau" |
| exon | 72 ... 221 |
| | /gene="tau" |
| | /number=1 |

BASE COUNT 61 a 80 c 69 g 49 t.
ORIGIN
1 CTCTCTCTCT CTTCACCCCA CTCTGCCCCC CAACACTCCT CAGAACTTAT CCTCTCCTCT
61 TCTTTCCCCA GGTGAACMTTGAACCAGGAT GGCTGAGCCC CGCCAGGAGT TCGAAGTGAT
121 GGAAGATCAC GCTGGGACGT ACGGGTTGGG GGACAGGAAA GATCAGGGGG GCTACACCAT
181 GCACCAAGAC CAAGAGGGTG ACACGGACGC TGGCCTGAAA GGTTAGTGGA CAGCCATGCA
241 CAGCAGGCCC AGATCACTG (SEQ ID NO: 9)
LOCUS HSAPTAU03 593 bp DNA PRI 25-FEB-1998
DEFINITION Homo sapiens microtubule-associated protein tau (tau) gene, exon 2.
ACCESSION AF047856L35768
VERSION AF047856.1 GI:2898164
SEGMENT 3 of 15
SOURCE human.
  ORGANISM Homo sapiens
    Eukaryota; Metazoa; Chordata; Craniata; Vertebrata; Mammalia;
    Eutheria; Primates; Catarrh Hominidae; Homo.
REFERENCE 1 (bases 1 to 593)
  AUTHORS Andreadis, A., Brown, W. M. and Kosik, K. S.
  TITLE Structure and novel exons of the human tau gene
  JOURNAL Biochemistry 31 (43), 10626–10633 (1992)
  MEDLINE 93041757

REFERENCE 2 (bases 1 to 593)
  AUTHORS Andreadis, A., Broderick, J. A. and Kosik, K. S.
  TITLE Relative exon affinities and suboptimal splice site signals lead to non-equivalence of two cassette exons
  JOURNAL Nucleic Acids Res. 23 (17), 3585–3593 (1995)
  MEDLINE 96032855
REFERENCE 3 (bases 1 to 593)
  AUTHORS Andreadis, A.
  TITLE Direct Submission
  JOURNAL Submitted (13-FEB-1998) Biomedical Sciences, Shriver Center, 200 Trapelo Road, Waltham, Mass. 02154, USA
COMMENT On Feb. 24, 1998 this sequence version replaced gi:1160939.

| FEATURES | Location/Qualifiers |
|---|---|
| source | 1 . . . 593 |
| | /organism="Homo Sapiens" |
| | /db_xref="taxon:9606" |
| | /chromosome="17" |
| | /map="17q21" |
| | /cell_type="white blood cell" |
| | /dev_stage="adult" |
| exon | 159 . . . 245 |
| | /gene="tau" |
| | /note="adult-specific cassette" |
| | /number=2 |

BASE COUNT 97 a 196 c 162 g 138 t
ORIGIN
1 TTGGTCCCTT TGTGGGTTTG TTGCAGGGCG TGT-TCCAGT GTTTCCACAG GGAGCGATTT
61 TCAGCTCCAC AGGACACTGC TCCCCAGTTC CTCCTGAGAA CAAAAGGGGG GCGCTGGGGA
121 GAGGCCACCG TTCTGAGGGC TCACTGTATG TGTTCCAGAA TCTCCCCTGC AGACCCCCAC
181 TGAGGACGGA TCTGAGGAAC CGGGCTCTGA AACCTCTGAT GCTAAGAGCA CTCCAACAGC
241 GGAAGGTGGG CCCCCCTTCA GACGCCCCCT CCATGCCTCC AGCCTGTGCT TAGCCGTGCT
301 TTGAGCCTCC CTCCTGGCTG CATCTGCTGC TCCCCCTGGC TGAGAGATGT GCTCACTCCT
361 TCGGTGCTTT GCAGGACAGC GTGGTGGGAG CTGAGCCTTG CGTCGATGCC TTGCTTCGCTG
421 GTGCTGAGTG TGGGCACCTT CATCCCGTGT GTGCTCTGGA GGCAGCCACC CTTGGACAGT
481 CCGGCGCACA GCTCCACAAA GCCCCGGTCC ATACGATTGT CCTCCCACAC CCCCTTCAAA
541 AGCCCCCTCC CTCCTCTCTT TCTTCAGGGG CCAGTAGGTC AGAGCAGCCA TTT (SEQ ID NO: 1
LOCUS HSAPTAU04 706 bp DNA PRI 25-FEB-1998
DEFINITION Homo sapiens microtubule-associated protein tau (tau) gene, exon 3.
ACCESSION AF047857 L35769
VERSION AF047857.1I GI:2898165
SEGMENT 4 of 15
SOURCE human.
  ORGANISM Homo sapiens
    Eukaryota; Metazoa; Chordata; Craniata; Vertebrata; Mammalia;
    Eutheria, Primates; Catarrhini; Hominidae; Homo.

REFERENCE 1 (bases 1 to 706)
  AUTHORS Andreadis, A., Brown, W. M. and Kosik, K.S.
  TITLE Structure and novel exons of the human tau gene
  JOURNAL Biochemistry 31(43), 10626–10633 (1992)
  MEDLINE 93041757
REFERENCE 2 (bases 1 to 706)
  AUTHORS Andreadis, A., Broderick, J. A. and Kosik, K. S.
  TITLE Relative exon affinities and suboptimal splice site signals lead to non-equivalence of two cassette exons
  JOURNAL Nucleic Acids Res. 23 (17), 3585–3593 (1995)
  MEDLINE 96032855
REFERENCE 3 (bases 1 to 706)
  AUTHORS Andreadis, A.
  TITLE Direct Submission
  JOURNAL Submitted (13-FEB-1998) Biomedical Sciences, Shriver Center, 200 Trapelo Road, Waltham, Mass. 02154, USA
COMMENT On Feb. 24, 1998 this sequence version replaced gi:1160940.

| FEATURES | Location/Qualifiers |
|---|---|
| source | 1 . . . 706 |
| | /organism="Homo sapiens" |
| | /db_xref="taxon:9606" |
| | /chromosome="17" |
| | /map="17q21" |
| | /cell_type="white blood cell" |
| | /dev_stage="adult" |
| exon | 495 . . . 581 |
| | /gene="tau" |
| | /note="adult-specific cassette" |
| | /number=3 |

BASE COUNT 154 a 193 c 203 g 156 t
ORIGIN
1 GGGAGAAGTC TTGGAAGTCA CCTAGAGATG ACACTGCCAT TTTGCAGATG AGGAAACCGT
61 CCAATCAAAA TGGACCAAGG ACTTGCCCAA AGCCTCACAG CAAAACCATA GGCCCCCGCA
121 CTAACCCCAG AGTCCCTGTG CTGTCTTAAG AATCAAATAG TTGTAAGCAA TCATCTGGTT
181 TTCAGTATTT CTTCTTTTAA AATGCCTGGG GCCATGCAGC AGTCTGTTGC ACTGCAGCGT
241 TTACACAGGG CTGCCGGGCT TTCCTGGTGG ATGAGCTGGG CGTTCATGAG CCAGAACCAC
301 TCAGCAGCAT GTCAGTGTGC TTCCTGGGGA GACTGGTAGC AGGGGCTCC GGGCCTACTTC
361 AGGGCTGCTT TCTGGCATAT GGCTGATCCC CTCCTCACTC CTCCTCCCTG CATGCTCCT
421 GCGCAAGAAG CAAAGGTGAG GGGCTGGGTA TGGCTCGTCC TGCCCCTCT AAGGTGGATC
481 TCGGTGGTTT CTAGATGTGA CAGCACCCTT AGTGGATGAG GGAGCTCCCG GCAAGCAGGC
541 TGCCGCGCAG CCCCACACGG AGATCCCAGA AGGAACCACA GGTGAGGGTA AGCCCCAGAG
601 ACCCCCAGGC AGTCAAGGCC CTGCTGGGTG CCCCAGCTGA CCGTGACAG AAGTGAGGGA
661 GCTTTGCGTG TTTATCCTCC TGTGGGGCAG GAACATGGGT GGATYC (SEQ ID NO: 11)
LOCUS HSAPTAU05 447 bp DNA PRI 25-FEB-1998
DEFINITION Homo sapiens microtubule-associated protein tau (tau) gene, exon 4.
ACCESSION AF027492

VERSION AF027492.1 GI:2598173
SEGMENT 5 of 15
SOURCE human.
   ORGANISM *Homo sapiens*
      Eukaryota; Metazoa; Cordata; Craniata; Vertebrata; Mammalia; Eutheria; Primates; Catarrhini; Hominidae; Homo.
REFERENCE 1 (bases 1 to 447)
   AUTHORS Andreadis, A., Brown, W. M. and Kosik, K. S.
   TITLE Structure and novel exons of the human tau gene
   JOURNAL Biochemistry 31(43), 10626–10633 (1992)
   MEDLINE 93041757
REFERENCE 2 (bases 1 to 447)
   AUTHORS Andreadis, A.
   TITLE Direct Submission
   JOURNAL Submitted (13-FEB-1998) Biomedical Sciences, Shriver Center, 200 Trapelo Road, Waltham, Mass. 02154, USA

| FEATURES | Location/Qualifiers |
|---|---|
| source | 1 . . . 447 |
| | /organism="*Homo sapiens*" |
| | /db_xref="taxon:9606" |
| | /chromosome="17" |
| | /map="17q21" |
| | /cell_type="white blood cell" |
| | /dev_stage="adult" |
| exon | 180 . . . 245 |
| | /gene="tau" |
| | /number=4 |

BASE COUNT 116 a 92 c 120 g 119 t
ORIGIN
1 GAACTCCTCA GCAATGACAT TTGCAGAGAA GCCAGAGCTG AGGGCAACCT TGGTATFCTT
61 GGGATGTGAA CTTTCCTGAA TGTMTAAGGG AAAATGCCCG AAGGTACAGA GAGCTTGGTT
121TCTAGTAAAT AATAACTGTC TTGCTTTTAC CCCCCTTCAT TTGCTGACAC ATACACCAGC
181 TGAAGAAGCA GGCATTGGAG ACACCCCAG CCTGGAAGAC GAAGCTGCTG GTCACGTGAC
241 CCAAGGTCAG TGAACTGGAA TTGCCTGCCA TGACTTGGGG GTTGGGGGGA GGGACATGGG
301 GTGGGCTCTG CCTGAAAAGA TCATTTGGAC CTGAGCTCTA ATCACAAGT CCAGGAGATT
361TAGGGAGTT GGTTCTTATC AAAGGTTGGC TACTCAGATA TAGAAAGCCC TAGTGGTTTT
421 TTCTAATAC CATTTCTGGG TATCATG (SEQ ID NO: 12)
LOCUS HSAPTAU06 954 bp DNA PRI 25-FEB-1998
DEFINITION *Homo sapiens* microtubule-associated protein tau (tau) gene, exon 4A.
ACCESSION AF047858 M93652
VERSION AF047858.1 GI:2898166
SEGMENT 6 of 15
SOURCE human.
   ORGANISM *Homo sapiens*
      Eukaryota; Metazoa; Chordata; Craniata; Vertebrata; Mammalia; Eutheria; Primates; Catarrhini; Hominidae; Homo.
REFERENCE 1 (bases 1 to 954)
   AUTHORS Andreadis, A., Brown, W. M. and Kosik, K. S.
   TITLE Structure and novel exons of the human tau gene
   JOURNAL Biochemistry 31 (43), 10626–10633 (1992)
   MEDLINE 93041757
REFERENCE 2 (bases 1 to 954)
   AUTHORS Andreadis, A.
   TITLE Direct Submission
   JOURNAL Submitted (13-FEB-1998) Biomedical Sciences, Shriver Center, 200 Trapelo Road, Waltham, Mass. 02154, USA
COMMENT On Feb. 24, 1998 this sequence version replaced gi:338682.

| FEATURES | Location/Qualifiers |
|---|---|
| source | 1 . . . 954 |
| | /organism="*Homo sapiens*" |
| | /db_xref="taxon:9606" |
| | /chromosome="17" |
| | /map="17q21" |
| | /cell_type="white blood cell" |
| | /dev_stage="adult" |
| exon | 62 . . . 814 |
| | /gene="tau" |
| | /note ="4A; peripheral-specific cassette" |

BASE COUNT 190 a 330 c 293 g 141 t
ORIGIN
1 GACTGGGCCG AGAAGGGTCC GGCCTTTCCG AAGCCCGCCA CCACTGCGTA TCTCCACACA
61 GAGCCTGAAA GTGGTAAGGT GGTCCAGGAA GGCTTCCTCC GAGAGCCAGG CCCCCCAGGT
121 CTGAGCCACC AGCTCATGTC CGGCATGCCT GGGGCTCCCC TCCTGCCTGA GGGCCCCAGA
181 GAGGCCACAC GCCAACCTTC GGGGACAGGA CCTGAGGACA CAGAGGGCGG CCGCCACGCC
241 CCTGAGCTGC TCAAGCACCA GCTTCTAGGA GACCTGCACC AGGAGGGGCC GCCGCTGAAG
301 GGGGCAGGGG GCAAAGAGAG GCCGGGGAGC AAGGAGGAGG TGGATGAAGA CCGCGACGTC
361 GATGAGTCCT CCCCCCAAGA CTCCCCTCCC TCCAAGGCCT CCCCAGCCCA AGATGGGCGG
421 CCTCCCCAGA CAGCCGCCAG AGAAGCCACC AGCATCCCAG GCTTCCCAGC GGAGGGTGCC
481 ATCCCCCTCC CTGTGGATTT CCTCTCCAAA GITTCCACAG AGATCCCAGC CTCAGAGCCC
541 GACGGGCCCA GTGTAGGGCG GGCCAAAGGG CAGGATGCCC CCCTGGAGTT CACGtttCAC
601 GTGGAAATCA CACCCAACGT GCAGAAGGAG CAGGCGCACT CGGAGGAGCA TTTGGGAAGG
661 GCTGCATTTC CAGGGGCCCC TGGAGAAGGGG CCAGAGGCCC GGGGCCCCTC TTTGGGAGAG
721 GACACAAAAG AGGCTGACCT TCCAGAGCCC TCTGAAAAGC AGCCTGCTGC TGCTCCGCGG
781 GGGAAGCCCG TCAGCCGGGT CCCTCAACTC AAAGGTCTGT GTCTTGAGCT TCTTCGCTCC
841 TRCCCTGGGG ACCTCCCAGG CCTCCCAGGC TGCGGGCACT GCCACTGAGC TTCCAGGCCT
901 CCCGACTCCT GCTGCTTCTG ACGTTCCTAG GACGCCACTA AATCGACACC TGGG (SEQ ID NO: 13)
LOCUS HSAPTAU07 180 bp DNA PRI 25-FEB-1998
DEFINITION *Homo sapiens* microtubule-associated protein tau (tau) gene, exon 5.
ACCESSION AF027493
VERSION AF027493.1 GI:2598175
SEGMENT 7 of 15
SOURCE human.

ORGANISM *Homo sapiens*
  Eukaryota; Metazoa; Chordata; Craniata; Vertebrata; Mammalia; Eutheria; Primates; Catarrhini; Hominidae; Homo.
REFERENCE 1 (bases 1 to 180)
  AUTHORS Ahdreadis, A., Brown, W. M. and Kosik, K. S.
  TITLE Structure and novel exons of the human tau gene
  JOURNAL Biochemistry 31 (43), 1062610633 (1992)
  MEDLINE 93041757
REFERENCE 2 (bases 1 to 180)
  AUTHORS Andreadis, A.
  TITLE Direct Submission
  JOURNAL Submitted (13-FEB-1998) Biomedical Sciences, Shriver Center, 200 Trapelo Road, Waltham, Mass. 02154, USA

| FEATURES | Location/Qualifiers |
|---|---|
| source | 1 . . . 180<br>/organism="*Homo sapiens*"<br>/db_xref="taxon:9606"<br>/chromosome="17"<br>/map="17q21"<br>/cell_type="white blood cell"<br>/dev_stage="adult" |
| exon | 62 . . . 117<br>/gene="tau"<br>/number=5 |

BASE COUNT 55 a 31 c 48 g 46 t
ORIGIN
1 TGGCTTTCTG TGAACAGTGA AAATGGAGTG TGA-CAAGCAT TCTTATTTTA TATTTATCA
61 GCTCGCATGG TCAGTAAAAG CAAAGACGGG ACTGGAAGCG ATGACAAAAA AGCCAAGGTA
121 AGCTGACGAT GCCACGGAGC TCTGCAGCTG GTCAAGTTTA CAGAGAAGCT GTCTTTATG (SEQ ID NO: 14)
LOCUS HSAPTAU08 457 bp DNA PRI 25-FEB-1998
DEFINITION *Homo sapiens* microtubule-associated protein tau (tau) gene, exon 6.
ACCESSION AF047859 X61371 S48149
VERSION AF047859.1 GI:2898167
SEGMENT 8 of 15
SOURCE human.
  ORGANISM *Homo sapiens*
    Eukaryota; Metazoa; Chordata; Craniata; Vertebrata; Mammalia; Eutheria; Primates; Catarrhini; Hominidae; Homo.
  REFERENCE 1 (bases 1 to 457)
    AUTHORS Andreadis, A., Brown, W. M. and Kosik, K. S.
    TITLE Structure and novel exons of the human tau gene
    JOURNAL Biochemistry 31 (43), 10626–10633 (1992)
    MEDLINE 93041757
  REFERENCE 2 (bases 1 to 457)
    AUTHORS Andreadis, A., Nisson, P. E., Kosik, K. S. and Watkins, P. C.
    TITLE The exon trapping assay partly discriminates against alternatively spliced exons
    JOURNAL Nucleic Acids Res. 21 (9), 2217–2221 (1993)
    MEDLINE 93275752
  REFERENCE 3 (bases 1 to 457)
    AUTHORS Andreadis, A.
    TITLE Direct Submission
    JOURNAL Submitted (13-FEB1998) Biomedical Sciences, Shriver Center, 200 Trapelo Road, Waltham, Mass. 02154, USA
  COMMENT On Feb. 24, 1998 this sequence version replaced gi:36716 gi:259205.

| FEATURES | Location/Qualifiers |
|---|---|
| source | 1 . . . 457<br>/organism="*Homo sapiens*"<br>/db_xref="taxon:9606"<br>/chromosome="17"<br>/map="17q21"<br>/cell_type="white blood cell"<br>/dev_stage="adult" |
| exon | 240 . . . 437<br>/gene="tau"<br>/note="cassette, complex expression pattern"<br>/number=6 |

BASE COUNT 122 a 118 c 80 g 137 t
ORIGIN
1 GAGCCCGTCT CAAAAAGAAA AAGCAAAAGA AAAAGAACTG TGATTGGGAG GAACGGTCAA
61 CTTTCCTGTT CTTACTGATC AGAAGGGATA TTAAGGGTAC CTGATTCAAA CAGCCTGGAG
121 TACACTGACT TTCAACCATT ACCTGCCTA TTTATTTTA GTTACTGTCC TTTTTTCAGT
181 TTGTTTCCCT CCTCCATGTG CTGACTTTTA TTTTGATTTT ATTTATGTTT ATGTTTAAGA
241 CATCCACACG TCCTCTGCT AAAACCTTGA AAAATAGGCC TGCCTTAGC CCCAAACTCC
301 CCACTCCTGG TAGCTCAGAC CCTCTGATCC AACCCTCCAG CCCTGCTGTG TGCCCAGAGC
361 CACCTTCCTC TCCTAAACAC GTCTCCTG TCACTTCCCG AACTGGCAGT TCTGGAGCAA
421 AGGAGATGAA ACTCAAGGTA AGGAAACTCT TTGAAAA (SEQ D NO: 15)
LOCUS HSAPTAU09 271 bp DNA PRI 25-FEB-1998
DEFINITION *Homo sapiens* microtubule-associated protein tau (tau) gene, exon 7.
ACCESSION AF047860 X61372
VERSION AF047860.1 GI:2898168
SEGMENT 9 of 15
SOURCE human.
  ORGANISM *Homo sapiens*
    Eukaryota;, Metazoa; Chordata; Craniata; Vertebrata; Mammalia; Eutheria; Primates; Catarrhini; Hominidae; Homo.
  REFERENCE 1 (bases 1 to 271)
    AUTHORS Andreadis, A., Brown, W. M. and Kosik, K. S.
    TITLE Structure and novel exons of the human tau gene
    JOURNAL Biochemistry 31 (43), 10626–10633 (1992)
    MEDLINE 93041757
  REFERENCE 2 (bases 1 to 271)
    AUTHORS Andreadis, A.
    TITLE Direct Submission
    JOURNAL Submitted (13-FEB-1998) Biomedical Sciences, Shriver Center, 200 Trapelo Road, Waltham, Mass. 02154, USA
  COMMENT On Feb. 24, 1998 this sequence version replaced gi:36718.

| FEATURES | Location/Qualifiers |
|---|---|
| source | 1 ... 271<br>/organism="*Homo sapiens*"<br>/db_xref="taxon:9606"<br>/chromosome="17"<br>/map="17q21"<br>/cell_type="white blood cell"<br>/dev_stage="adult" |
| exon | 134 ... 260<br>/gene="tau"<br>/number=7 |

BASE COUNT 69 a 79 c 74 g 49 t
ORIGIN
1 TCTAGGAGGC CAAGGGTCAC CCCAGTCTTA GCCACGTTT GAGTCAAGGT GGCGGAGTGG
61 GGCTGGTGTT ACGTCTTGGT GGCAGTAACT TTTCCCAATG GTGAAAAACC CCTCTATCAT
121 GTTTCATTA CAGGGGGCTG ATGGTAAAAC GAAGATCGCC ACACCGCGGG GAGCAGCCCC
181 TCCAGGCCAG AAGGGCCAGG CCAACGCCAC CAGGATYCCA GCAAAACCC CGCCCGCTCC
241 AAAGACACCA CCCAGCTCTG GTAAGAAGAA C
(SEQ ED NO: 16)
LOCUS HSAPTAU10 150 bp DNA PRI 25-FEB-1998
DEFINITION *Homo sapiens* microtubule-associated protein tau (tau) gene, exon 8.
ACCESSION AF047861 X61375 S48175
VERSION AF047861.1 GI:2898169
SEGMENT 10 of 15
SOURCE human.
   ORGANISM *Homo sapiens*
      Eukaryota; Metazoa; Chordata; Craniata; Vertebrata; Mammalia; Eutheria; Primates; Catarrhini; Hominidae; Homo.
REFERENCE 1 (bases 1 to 150)
   AUTHORS Andreadis, A., Brown, W. M. and Kosik, K. S.
   TITLE Structure and novel exons of the human tau gene
   JOURNAL Biochemistry 31 (43), 10626–10633 (1992)
   MEDLINE 93041757
REFERENCE 2 (bases 1 to 150)
   AUTHORS Andreadis, A.
   TITLE Direct Submission
   JOURNAL Submitted (13-FEB-1998) Biomedical Sciences, Shriver Center, 200 Trapelo Road, Waltham, Mass. 02154, USA
COMMENT On Feb. 24, 1998 this sequence version replaced gi:36720 gi:259206.

| FEATURES | Location/Qualifiers |
|---|---|
| source | 1 ... 150<br>/organism="*Homo sapiens*"<br>/db_xref="taxon:9606"<br>/chromosome="17"<br>/map="17q21"<br>/cell_type="white blood cell"<br>/dev_stage="adult" |
| exon | 68 ... 121<br>/gene="tau"<br>/note="cassette, unclear expression pattern"<br>/number=8 |

BASE COUNT 39 a 36 c 41 g 34 t
ORIGIN
1 GAAGGACTCA TAAGGCCCT GTTAAGCCT GATGATAATA AGGCTTTCGT GGATTTTTCT
61 CTTAAGCGA CTAAGCAAGT CCAGAGAAGA CCACCCCTG CAGGGCCCAG ATCTGAGAGA
121 GGTACTCGGG AGCCTACTCG CTGGGAGCAG
(SEQ ID NO: 17)
LOCUS HSAPTAU11 637 bp DNA PRI 25-FEB-1998
DEFINITION *Homo sapiens* microtubule-associated protein tau (tau) gene, exon 9.
ACCESSION AF047862 X61374
VERSION AF047862.1 GI:2898170
SEGMENT 11 of 15
SOURCE human.
   ORGANISM *Homo sapiens*
      Eukaryota; Metazoa; Chordata; Craniata; Vertebrata; Mammalia; Eutheria; Primates; Catarrhini; Hominidae; Homo.
REFERENCE 1 (bases 1 to 637)
   AUTHORS Andreadis, A., Brown, W. M. and Kosik, K. S.
   TITLE Structure and novel exons of the human tau gene
   JOURNAL Biochemistry 31 (43), 10626–10633 (1992)
   MEDLINE 93041757
REFERENCE 2 (bases 1 to 637)
   AUTHORS Andreadis, A.
   TITLE Direct Submission
   JOURNAL Submitted (13-FEB-1998) Biomedical Sciences, Shriver Center, 200 Trapelo road, Waltham, Mass. 02154, USA
COMMENT On Feb. 24, 1998 this sequence version replaced gi:36722.

| FEATURES | Location/Qualifiers |
|---|---|
| source | 1 ... 637<br>/organism="*Homo sapiens*"<br>/db_xref="taxon:9606"<br>/chromosome="17"<br>/map="17q21"<br>/cell_type="white blood cell"<br>/dev_stage="adult" |
| exon | 357 ... 622<br>/gene="tau"<br>/number=9 |

BASE COUNT 124 a 211 c 179 g 116 t 7 others
ORIGIN
1 GAGCTCAGAG AGGGGAAGTTACTTGTCTGA GGCCACACAG CTGTTGGAG CCCATCTCTT
61 GACCCAAAGA CTGTGGAGCC GAGTTGGCAC CTCTCTGGGA GCGGGTATTG GATGGTGGTT
121 GATGGTTTTC CATTGCTUC CTGGGAAAGG GGTGTCTCTG TCCCTCCGCA AAAGGACAG
181 GGAGGAAGAG ATGCTTCCCC AGGGCNNNNG TCTGCTGTAC GTGCGCTTCC AACCTGGCTT 241 CCACCTGCCT AACCCAGTGG TGAGCCTGGG
AATGGACCCA CGGGACAGGN NNCCCCAGGG
301 CCTTTCTGA CCCCACCCAC TCGAGTCCTG GCT-
TCACTCC CTTCCTTCCT TCCCAGGTGA
361 ACCTCCAAAA TCAGGGGATC GCAGCGGCTA
CAGCAGCCCC GGCTCCCAG GCACTCCCGG
421 CAGCCGCTCC CGCACCCGT CCCTTCCAAC
CCCACCCACC CGGGAGCCCA AGAAGOTGGC
481 AGTGGTCCGT ACTCCACCCA AGTCGCCGTC
TTCCGCCAAG AGCCGCCTGC AGACGCCCC
541 CGTGCCCATG CCAGACCTGA AGAATGTCAA
GTCCAAGATC GGCTCCACTG AGAACCTGAA
601 GCACCAGCCG GGAGGCGGGA AGGTGAGAGT
GGCTGGC (SEQ ID NO: 18)
LOCUS HSAPTAU12 222 bp DNA PRI 25-FEB-1998
DEFINITION *Homo sapiens* microtubule-associated protein tau (tau) gene, exon 10.
ACCESSION AF027494
VERSION AF027494.1 GI:2598177
SEGMENT 12 of 15
SOURCE human.
  ORGANISM *Homo sapiens*
    Eukaryota; Metazoa; Chordata; Craniata; Vertebrata; Mammalia; Eutheria; Priamtes; Catarrhini; Hominidae; Homo.
REFERENCE 1 (bases 1 to 222)
  AUTHORS Andreadis, A., Brown, W. M. and Kosik, K. S.
  TITLE Structure and novel exons of the human tau gene
  JOURNAL Biochemistry 31 (43), 10626–10633 (1992)
  MEDLINE 93041757
REFERENCE 2 (bases 1 to 222)
  AUTHORS Andreadis, A.
  TITLE Direct Submission
  JOURNAL Submitted (13-FEB-1998) Biomedical Sciences, Shriver Center, 200 Trapelo Road, Waltham, Mass. 02154, USA

| FEATURES | Location/Qualifiers |
|---|---|
| source | 1 ... 222 |
| | /organism="*Homo sapiens*" |
| | /db_xref="taxon:9606" |
| | /chromosome="17" |
| | /map="17q21" |
| | /cell_type="white blood cell" |
| | /dev_stage="adult" |
| exon | 59 ... 151 |
| | /gene="tau" |
| | /note="adult-specific cassette" |
| | /number=10 |

BASE COUNT 55 a 51 c 63 g 53 t
ORIGIN
1 CGAGCAAGCA GCGGGTCCAG GGTGGCGTGT
CACTCATCCT TTTTTCTGGC TACCAAGGT
61 GCAGATAATT AATAAGAAGC TGGATCATAG
CAACGTCCAG TCCAAGTGTG GCTCAAAGGA
121 TAATATCAAA CACGTCCCGG GAGGCGGCAG
TGTGAGTACC TTCACACGTC CCATGCGCCG
181 TGCTGTGGCT TGAATTATTA GGAAGTGGTG
TGAGTCGTAC AC (SEQ ID NO. 19)
LOCUS HSAPTAU13 246 bp DNA PRI 25-FEB-1998
DEFINITION *Homo sapiens* microtubule-associated protein tau (tau) gene, exon 11.

ACCESSION AF027495
VERSION AF027495.1 GI:2598179
SEGMENT 13 of 15
SOURCE human.
  ORGANISM *Homo sapiens*
    Eukaryota; Metazoa; Chordata; Craniata; Vertebrata; Mammalia; Eutheria; Primates; Catarrhini; Hominidae; Homo.
REFERENCE 1 (bases 1 to 246)
  AUTHORS Andreadis, A., Brown, W. M. and Kosik, K. S.
  TITLE Structure and novel exons of the human tau gene
  JOURNAL Biochemistry 31(43), 10626–10633 (1992)
  MEDLINE 93041757
REFERENCE 2 (bases 1 to 246)
  AUTHORS Andreadis, A.
  TITLE Direct Submission
  JOURNAL Submitted (13-FEB-1998) Biomedical Sciences, Shriver Center, 200 Trapelo Road, Waltham, Mass. 02154, USA

| FEATURES | Location/Qualifiers |
|---|---|
| source | 1 ... 246 |
| | /organism="*Homo sapiens*" |
| | /db_xref="taxon:9606" |
| | /chromosome="17" |
| | /map="17q21" |
| | /cell_type="white blood cell" |
| | /dev_stage="adult" |
| exon | 35 ... 116 |
| | /gene="tau" |
| | /number=11 |

BASE COUNT 63 a 55 c 72 g 56 t
ORIGIN
1 TTGCTCATTC TCTCTCCTCC TCTCTCATCT CCAG-
GTGCAA ATAGTCTACA AACCAGTTGA
61 CCTGAGCAAG GTGACCTCCA AGTGTGGCTC
ATAGGCAAC ATCCATCATA AACCAGGTAG
121 CCCTGTGGAA GGTGAGGGT GGGACGGGAG
GTGCAGGGG GTGGAGGAGT CCTGGTGAGG
181 CTGGAACTGC TCCAGACTTC AGAAGAGGCT
GGAAAGGATA TTTTAGGTAG ACCTACATCA
241AGGAAA(SEQ ID NO: 20)
LOCUS HSAPTAU14 200 bp DNA PRI 25-FEB-1998
DEFINITION *Homo sapiens* microtubule-associated protein tau (tau) gene, exon 12.
ACCESSION AF027496
VERSION AF027496.1 GI:2598181
SEGMENT 14 of 15
SOURCE human.
  ORGANISM *Homo sapiens*
    Eukaryota; Metazoa; Chordata; Craniata; Vertebrata; Mammalia; Eutheria; Primates; Catarrhini; Hominidae; Homo.
REFERENCE 1 (bases 1 to 200)
  AUTHORS Andreadis, A., Brown, W. M. and Kosik, K. S.
  TITLE Structure and novel exons of the human tau gene
  JOURNAL Biochemistry 31 (43), 10626–10633 (1992)
  MEDLINE 93041757
REFERENCE 2 (bases 1 to 200)
  AUTHORS Andreadis, A.
  TITLE Direct Submission JOURNAL Submitted (13-FEB-1998) Biomedical Sciences, Shriver Center, 200 Trapelo Road, Waltham, Mass. 02154, USA

| FEATURES | Location/Qualifiers |
|---|---|
| source | 1 ... 200<br>/organism="Homo sapiens"<br>/db_xref="taxon:9606"<br>/chromosome="17"<br>/map="17q21"<br>/cell_type="white blood cell"<br>/dev_stage="adult" |
| exon | 55 ... 167<br>/gene="tau"<br>/number=12 |

BASE COUNT 55 a 36 c 65 g 44 t
ORIGIN
1 CCACAGAACC ACAGAAGATG ATGGCAAGAT GCTCTTGTGT GTGTTGTGTT CTAGGAGGTG
61 GCCAGGTGGA AGTAAAATCT GAGAAGCTTG ACCAAGGA CAGAGTCCAG TCGAAGATTG
121 GGTCCCTGGA CAATATCACC CACGTCCCTG GCGGAGGAAA TAAAAGGTA AAGGGGGTAG
181 GGTGGGTTGG ATGCTGCTT (SEQ ID NO: 21)
LOCUS HSAPTAU15 1498 bp DNA PRI 25-FEB-1998

DEFINITION Homo sapiens microtubule-associated protein tau (tau) gene, alternatively spliced products, exon 13/14 and complete cds.
ACCESSION AF047863 X61373 S48177
VERSION AF047863.1 GI:2898171
SEGMENT 15 of 15
SOURCE human.
  ORGANISM Homo sapiens
    Eukaryota; Metazoa; Chordata; Craniata; Vertebrata; Mammalia; Eutheria; Primates; Catarrhini; Hominidae; Homo.
REFERENCE i (bases 1 to 1498)
  AUTHORS Andreadis, A., Brown, W. M. and Kosik, K. S.
  TITLE Structure and novel exons of the human tau gene
  JOURNAL Biochemistry 31 (43), 10626-10633 (1992)
  MEDLINE 93041757
REFERENCE 2 (bases 1 to 1498)
  AUTHORS Andreadis, A.
  TITLE Direct Submission
  JOURNAL Submitted (13-FEB-1998) Biomedical Sciences, Shriver Center, 200 Trapelo Road, Waltham, Mass. 02154, USA
COMMENT On Feb. 24, 1998 this sequence version replaced gi:36714 gi:259207.

| FEATURES | Location/Qualifiers |
|---|---|
| source | 1 ... 1498<br>/organism = "Homo sapiens"<br>/db_ref = "taxon:9606"<br>/chromosome = "17"<br>/map = "17q21"<br>/cell_type = "white blood cell"<br>/dev_stage = "adult" |
| mRNA | join(AF047855.1:379 ... 597,AF027491.1:72 ... 221,<br>AF047856.1:159 ... 245,AF047857.1:495 ... 581,<br>AF027492.1:180 ... 245,AF047858.1:62 ... 814,AF027493.1:62 ... 117,<br>AF047859.1:240 ... 437,AF047860.1:134 ... 260,<br>AF047862.1:357 ... 622,AF027494.1:59 ... 151,AF027495.1:35 ... 116,<br>AF027496.1:55 ... 167,49 ... 1498)<br>/gene = "tau"<br>/product = "PNS specific microtubule-associated protein tau, adult isoform" |
| mRNA | join(AF047855.1:379 ... 597,AF027491.1:72 ... 221,<br>AF027492.1:180 ... 245,AF027493.1:62 ... 117,<br>AF047860.1:134 ... 260,AF047862.1:357 ... 622,<br>AF027495.1:35 ... 116,AF027496.1:55 ... 167,49 ... 1498)<br>/gene = "tau"<br>/product = "CNS specific microtubule-associated protein tau, fetal isoform" |
| mRNA | join(AF047855.1:379 ... 597,AF027491.1:72 ... 221,<br>AF047856.1:159 ... 245,AF047857.1:495 ... 581,<br>AF027492.1:180 ... 245,AF027493.1:62 ... 117,<br>AF047860.1:134 ... 260,AF047862.1:357 ... 622,<br>AF027494.1:59 ... 151,AF027495.1:35 ... 116,AF027490,1:55 ... 167,<br>49 ... 1498)<br>/gene = "tau"<br>/product = "CNS specific microtubule-associated protein tau, adult isoform" |
| gene | order(AF047855.1:379 ... 792,AF027490 ... 1:1 ... 259,<br>AF047856.1:1 ... 593,AF047857.1:1 ... 706,AF027492.1:1 ... 447,<br>AF047858.1:1 ... 954,AF027493.1:1 ... 180,AF047859.1:1 ... 457,<br>AF047860.1:1 ... 271,AF047861.1:1 ... 150,AF047862.1:1 ... 637,<br>AF027494.1:1 ... 222,AF027495.1:1 ... 246,AF027496.1:1 ... 200,<br>1 ... 1498)<br>/gene = "tau" |
| CDS | join(AF027491.1:89 ... 221,AF047856.1:159 ... 245,<br>AF047857.1:495 ... 581,AF027492.1:180 ... 245,<br>AF027493.1:62 ... 117,AF047860.1:134 ... 260,<br>AF047862.1:357 ... 622,AF027494.1:59 ... 151,AF027495.1:35 ... 116, |

| FEATURES | Location/Qualifiers |
|---|---|
| | AF027496.1:55 . . . 167,49 . . . 264)<br>/gene = "tau"<br>/codon_start = 1<br>/product = "CNS specific microtubule-associated protein tau, adult isoform"<br>/protein_id = "AAC04279.1"<br>/db_xref = "GI:2911249" |

/translation=
"MAEPRQEFEVMEDHAGTYGLGDRKDQG-
GYTMHQDQEGDTDAGLKESPLQTPTEDG-
SEEPGSETSDAKSTPTAEDVTAPLVDEGAPGKQA
AAQPHTEIPEGTTAEEAGIGDTPSLE-
DEAAGHVTQARMVSKSKDGTGSDDKKAK-
GADGKTKIATPRGAAPPGQKGQANATRI-
PAKTPPAPKTPPSSGEPPKSGDRSGYSSPGSPGT
PGSRSRTPSLPTPPTREPKKVAVVRTP-
PKSPSSAKSRLQTAPVPMPDLKNVK-
SKIGSTENLKHQPGGGKVQIINKLDLSN-
VQSKCGSKDNIKHVPGGGSVQIVYKPVDLSKVTS
KCGSLGNIHHKPGGGQVEVKSEKLD-
FKDRVQSKIG
SLDNITHVPGGGNKKIETHKLT-
FRENAKAKTDHGAEIVYKSPVVS-
GDTSPRHLSNVSSTGSIDMVDSPQLAT-
LADEVSASLAKQGL"

/translation=
"MAEPRQEFVMEDHAGTYGLGDRKDQG-
GYTMHQDQEGDTDAGLKAEEA-
GIGDTPSLEDEAAGHVTQARMVSKSKDGTGSDD
KKAKGADGKTKIATPRGAAP-
PGQKGQANATRIPAKTPPAPKTPPSS-
GEPPKSGDRSGYSSPGSPGTPG-
SRSRTPSLPTPPTREPKKVAVVRTPPKSPSSAKSR
LQTAPVPMPDLKNVKSKIGSTEN-
LKHQPGGGKVQIVYKPVDL-
SKVTSKCGSLGNIHHKPGGGQVEVKSEK-
LDFKDRVQSKIGSLDNITHVPGGGNKKIETHKL
TFRENAKAKTDHGAEIVYKSPVVS-
GDTSPRHLSNVSST
GSIDMVDSPQLATLADEVSASLAKQGL"

| CDS | join(AF027491.1:89 . . . 221,AF027492.1:180 . . . 245,<br>AF027493.1:62 . . . 117,AF047860.1:134 . . . 260,<br>AF047862.1:357 . . . 622,AF027495.1:35 . . . 116,AF027496.1:55 . . . 167,<br>49 . . . 264)<br>/gene = "tau"<br>/codon_start = 1<br>/product = "CNS specific microtubule-associated protein tau, fetal isoform"<br>/protein_id = "AAC04278.1"<br>/db_xref = "GI:29112483" |
|---|---|

| CDS | join(AF027491.1:89 . . . 221,AF047856.1:159 . . . 245,<br>AF047857.1:495 . . . 581,AF027492.1:180 . . . 245,<br>AF047858.1:62 . . . 814,AF027493.1:62 . . . 117,AF047859.1:240 . . . 437,<br>AF047860.1:134 . . . 260,AF047862.1:357 . . . 622,<br>AF027494.1:59 . . . 151,AF027495.1:35 . . . 116,AF027496.1:55 . . . 167,<br>49 . . . 264)<br>/gene = "tau"<br>/codon_start = 1<br>/product = "PNS specific microtubule-associated protein tau, adult isoform"<br>/protein_id = "AAC04277.1"<br>/db_xref "GI:2911247" |
|---|---|

/translation=
"MAEPRQEFEVMEDHAGTYGLGDRKDQG-
GYTMHQDQEGDTDAGLKESPLQTPTEDG-

SEEPGSETSDAKSTPTAEDVTAPLVDEGAPGK
QAAAQPHTEIPEGTTAEEAGIGDTPSLE-
DEAAGHVTQEPESGKVVQEGFLREPGP-
PGLSHQLMSGMPGAPLLPEGPRE-
ATRQPSGTGPEDTEGGRHAPELLKHQLLGDLH
QEGPPLKGAGGKERPGSKEEVDEDRD-
VDESSPQDSPPSKASPAQDGRPPQTAAR-
EATSIPGFPAEGAIPLPVDPLSKVSTEI-
PASEPDGPSVGRAKGQDAPLEFTFHVEITPNVQ
KEQAHSEEHLGRAAFPGAPGEGPE-
ARGPSLGEDTKEADLPEPSEKQ-
PAAAPRGKPVSRVPQLKARM-
VSKSKDGTGSDDKKAKTSTRSSAKTLKNRPCLS
PKLPTPGSSDPLIQPSSPAVCPEPPSSP-
KHVSSVTSRTGSSGAKEMKLKGADGKT-
KEATPRTAAPPGQKGQANATRIPAKTP-
PAPKTPPSSGEPPKSGDRSGYSSPGSPGTPGSRSR
TPSLPTPPTRBPKVAWRTPPKSPSSAK-
SRLQTAPVPMPDLKNVKSKIGSTEN-
LKHQPGGGKVQIINKKLDLSNVQSKCG-
SKDNIKHVPGGGSVQIVYPVDLSKVTSKCGSLG
NIHHKPGGGQVEVKSEKLD-
FKDRVQSKIGSLDNITHVPGGGNKKI-
ETHKLTFRENAKAKTDHGAEIVYKSPV-
VSGDTSPRHLSNVSSTGSIDMVDSPQLATLA
DEVSASLAKQGL"

| | |
|---|---|
| exon | 49 ... 1498 |
| | /gene = "tau" |
| | /note = 13/14; retained/excised intron; exon 14 is similar to murine tau exon 14" |
| intron | 257 ... 1189 |
| | /gene = "tau" |
| | /note = "spliced out only in small percentage of mRNAS" |

BASE COUNT 315a 401c 446g 336t
ORIGIN
1 CTTCTCTGG CACTRCATCT CACCCTCCCT CCCT-
   TCTCT TCTTGCAGAT TGAACCCAC
61 AAGCTGACCT TCCGCGAGAA CGCCAAAGCC
   AAGACAGACC ACGGGGCGGA GATCGTGTAC
121 AAGTCGCCAG TGGTGTCTGG GGACACGTCT
   CCACGGCATC TCAGCAATGT CTCCTCCACC
181 GGCAGCATCG ACATGGTAGA CTCGCCCCAG
   CTCGCCACGC TAGCTGACGA GGTGTCTCC
241 TCCCTGGCCA AGCAGGGT GTATCAGGC
   CCCTGGGGCG GTCAATAAT GTGGAGAGGA
301 GAGAATGAGA GAGTGTGGAA AAAAAAAGAA
   TAATGACCCG GCCCCCGCCC TCTGCCCCCA
361 GCTGCTCCTC GCAGTTCGGT TAATTGGTTA
   ATCACTTAAC CTGCTTTTGT CACTCGGCTT
421 TGGCTCGGGA CTTCAAAATC AGTGATGGGA
   GTAAGAGCAA ATTTCATCTT TCCAAATTGA

481 TGGGTGGGCT AGTAATAAAA TATTAAAAA
   AAAACATTCA AAAACATGGC CACATCCAAC
541 ATTTCCTCAG GCAATTCCTT TTGATTCTTT
   TTTCTTCCCC CTCCATGTAG AAGAGGGAGA
601 AGGAGAGGCT CTGAAAGCTG CTTCTGGGGG
   AmCAAGGG ACTGGGGGTG CCAACCACCT
661 CTGGCCTGT TGTGGGGGTT GTCACAGAGG
   CAGTGGCAGC AACAAAGGAT TTGAAAACTT
721 TGGTGTGTTC GTGGAGCCAC AGGCAGACGA
   TGTCAACCTT GTGTGAGTGT GACGGGGGTT
781 GGGGTGGGGC GGGAGGCCAC GGGGGAGGCC
   GAGCAGGGG CTGGGCAGAG GGGAGGAGGA
841 AGCACAAGAA GTGGGAGTGG GAGAGGAAGC
   CACGTGCTGG AGAGTAGACA TCCCCCTCCT
901 TGCCGCTGGG AGAGCCAAGG CCTATGCCAC
   CTGCAGCGTC TGAGCGGCCG CCTGTCCTTG
961 GTGGCCGGGG GTGGGGGCCT GCTGTGGGTC
   AGTGTGCCAC CCTCTGCAGG GCAGCCTGTG
1021 GGAGAAGGGA CAGCGGGTTA AAAAGAGAAG
   GCAAGCCTGG CAGGAGGGTT GGCACTTCGA
1081 TGATGACCTC CTTAGAAAGA CTGACCTTGA
   TGTCTTAGA GCGCTGGCCT CTCCTCCCT
1141 CCCTGCAGGG TAGGGCGCCT GAGCCTAGGC
   GGTTCCCTCT GCTCCACAGA AACCCTTT
1201 TATTGATTC TGAAGGTTGG AACTGCTGCC
   ATGATTTTGG CCACTTTGCA GACCTGGGAC
1261 TTTAGGGCTA ACCAGTTCTC TTGTAAGGA
   CTTGTGCCTC TTGGGAGACG TCCACCCGTT
1321 TCCAAGCCTG GGCCACTGGC ATCTCTGGAG
   TGTGTGTGGGG TCTGGGAGGC AGGTCCCGAG
1381 CCCCCTGTCC TrCCCACGGC CACTGCAGTC
   ACCCCGTC CGCCGCTGTG CTGTRGTCTG
1441 CCGTGAGAGC CCAATCACTG CCTATACCCC
   TCATCACACG TCACAATGTC CCGAATTC (SEQ ID NO: 22)

The foregoing is considered illustrative only of the principles of the present invention, since numerous modifications and changes will readily occur to those skilled in the art, it is not desired to limit the invention to the exact construction and operation shown and described. For example, while the present invention is explained primarily with reference to mice, it will be appreciated that the invention can be implemented with other mamnmalian species, such as rats, dogs, cats, pigs, rabbits and monkeys, in accordance with known techniques, or techniques that will be apparent to those skilled in the relevant arts. Accordingly, all suitable modifications and equivalents may be resorted to that fall within the scope of the invention and the appended claims.

The disclosures of U.S. Pat. Nos. 5,767,337; 5,569,827; 5,569,824 and 5,703,209 are expressly incorporated herein.

We claim:

1. A transgenic mouse having a genome comprising: (i) an inactive mouse TAU gene, and (ii) a transgene encoding either (a) the human TAU gene or (b) a mutated human TAU gene associated with FTDP-17, said transgene operatively linked to regulatory elements for neuronal expression of said transgene in said transgenic mouse, wherein said transgene expresses human Tau isoforms, and wherein said transgenic mouse develops Tau phosphorylation.

2. The mouse according to claim 1, wherein said genome contains one allele encoding the human TAU gene.

3. The mouse according to claim 1, wherein said genome contains two alleles encoding the human TAU gene.

4. A method of determining if a compound is capable of modulating an Alzheimer's like Tau pathology, comprising administering said compound to a mouse of claim 1, and then examining said mouse for modulation of Alzheimer's like Tau pathology characteristics.

5. A method of determining if a compound is capable of inducing an Alzheimer's like Tau pathology, comprising administering said compound to a mouse of claim 1, and then examining said mouse for development of Alzheimer's like Tau pathology characteristics.

6. A method of screening a compound for activity in treating an Alzheimer's like Tau pathology, comprising administering said compound to a mouse of claim 1, and then examining said mouse for the treatment of said Alzheimer's like Tau pathology.

7. A method of determining if a compound is capable of modulating at least one frontotemporal dementia or Parkinson's-like disease, comprising administering said compound to a mouse of claim 1, and then examining said mouse for modulation of characteristics of the disease.

8. A method of determining if a compound is capable of inducing at least one frontotemporal dementia or Parkinson's-like disease, comprising administering said compound to a mouse of claim 1, and then examining said mouse for the inducement of the disease.

9. A method of screening a compound for activity in treatment of at least one frontotemporal dementia disease or Parkinson's-like disease, comprising administering said compound to a mouse of claim 1, and then examining said mouse for the treatment of said disease.

10. A method of using the mouse of claim 1 to produce a human Tau protein, isoform of the protein, or mutated isoform of the protein, comprising the steps of:
   allowing the mouse to produce the protein; and
   removing the protein from the mouse.

11. A transgenic mouse whose germ cells and somatic cells contain an inactive mouse TAU gene, wherein Exon 1 of said inactive mouse TAU gene is deleted and replaced with an expression cassette having a heterologous gene operably linked with a promoter, being oriented in the opposite direction of transcription of said inactive mouse TAU gene, wherein said transgenic mouse is deficient in microtubule assembly and stabilization.

12. A transgenic mouse having a genome comprising a transgene encoding (a) the human TAU gene or (b) a mutated human TAU gene associated with FTDP-17, said transgene operatively linked to regulatory elements for neuronal expression of said transgene in said transgenic mouse, wherein said transgene expresses human Tau isoforms, and wherein said transgenic mouse develops Tau phosphorylation.

13. A method of determining if a compound is capable of modulating an Alzheimer's like Tau pathology, comprising administering said compound to a mouse of claim 12, and then examining said mouse for modulation of Alzheimer's like Tau pathology characteristics.

14. A method of determining if a compound is capable of inducing an Alzheimer's like Tau pathology, comprising administering said compound to a mouse of claim 12, and then examining said mouse for development of Alzheimer's like Tau pathology characteristics.

15. A method of screening a compound for activity in treating an Alzheimer's like Tau pathology, comprising administering said compound to a mouse of claim 12, and then examining said mouse for the treatment of said Alzheimer's like Tau pathology.

16. A method of determining if a compound is capable of modulating at least one frontotemporal dementia or Parkinson's-like disease, comprising administering said compound to a mouse of claim 12, and then examining said mouse for modulation of characteristics of the disease.

17. A method of determining if a compound is capable of inducing at least one frontotemporal dementia or Parkinson's-like disease, comprising administering said compound to a mouse of claim 12, and then examining said mouse for development of the disease.

18. A method for screening a compound for activity in treatment of at least one frontotemporal dementia disease or Parkinson's-like disease, comprising administering said compound to a mouse of claim 12, and then examining said mouse for the treatment of said disease.

19. A method of using the mouse of claim 12 to produce a human Tau protein, isoform of the protein, or mutated isoform of the protein, comprising the steps of:
   allowing the mouse to produce the protein; and
   removing the protein from the mouse.

* * * * *